(12) United States Patent  
McAlpine et al.

(10) Patent No.: US 7,312,339 B2  
(45) Date of Patent: Dec. 25, 2007

(54) POLYENE OXAZOLES AND PROCESSES FOR THEIR PREPARATION

(75) Inventors: James B. McAlpine, Montreal (CA); Chris M. Farnet, Outremont (CA); Emmanuel Zazopoulos, Montreal (CA); Nargis Ismail, Montreal (CA); Brian O. Bachmann, Nashville, TN (US)

(73) Assignee: Thallion Pharmaceuticals Inc., Montreal (CA)

( * ) Notice: Subject to any disclaimer, the term of this patent is extended or adjusted under 35 U.S.C. 154(b) by 536 days.

(21) Appl. No.: 10/865,767

(22) Filed: Jun. 14, 2004

(65) Prior Publication Data

US 2005/0038090 A1     Feb. 17, 2005

Related U.S. Application Data

(60) Provisional application No. 60/477,931, filed on Jun. 13, 2003.

(51) Int. Cl.  
C07D 207/444   (2006.01)  
C07D 209/48    (2006.01)

(52) U.S. Cl. ...................... 548/236; 514/374
(58) Field of Classification Search ................ 548/236  
See application file for complete search history.

(56) References Cited

U.S. PATENT DOCUMENTS

| 3,854,480 A | 12/1974 | Zaffaroni |
| 4,452,775 A | 6/1984 | Kent |
| 5,039,660 A | 8/1991 | Leonard |

OTHER PUBLICATIONS

Otani T. et al., The Journal of Antibiotics (2000)vol. 53, No. 12 pp. 1397-1400☐☐"Novel Triene-b-lactone Antibiotics, Oxazolomycin Derivative and Its Isomer, Produced by *Streptomyces* sp. KSM-2690".*  
Berge et al., Journal of Pharmaceutical Sciences, (1977) 66:2 pp. 1-19 "Pharmaceutical Salts".  
Goodfellow, Bergey's Manual of Systematic Bactreiology, (1989) vol. 4, Williams and Wilkins, Baltimore, pp. 2322-2339 "Supragenetic classification of actinomycetes".  
Embley and Stackebrandt, Annu. Rev. Microbiol., (1994) vol. 48, pp. 257-289 "The molecular phylogeny and systematics of the actinomycetes".  
Ogura et al., J. Antibiotics, (1985) vol. 38, No. 5, pp. 669-673 "Structure of a new antibiotic curromycin A produced by a genetically modified strain of *Streptomyces hygroscopicus*, a polyether antibiotic producing organism".  
Ogura M. et al., Agric. Biol. Chem., (1985)vol. 49, No. 6, pp. 1909-1910 "Isolation and structural determination of a new antibiotic Curromycin B" .  
Kansaki H. et al., Biosc. Biotechnol. Biochem., (1998) vol. 62, No. 3, pp. 438-442 "Novel bioactive oxazolomycin isomers produced by *Streptomyces albus* JA3453".  
Mori et al., Tetra hedron Letters, (1985) vol. 26, No. 8, pp. 1073-1076 "Structure of oxazolomycin, a novel beta-lacton antibiotic".  
Tonew et al., Acta Virol., (1992) vol. 36, pp. 166-177 "On the antiviral activity of diffusomycin (oxazolomycin)".  
Okabe T. et al., The Journal of Antibiotics (1985) vol. 38, No. 7, pp. 964-965 "IM8443T Substance, an antitumor trieneβ-lactone antibiotic".  
Ikeda Y. et al., The Journal of Antibiotics (1990) vol. 44, No. 4 pp. 453-455 "New triene β-lactone antibiotics, triedimycins A and B".  
Otani T. et al., The Journal of Antibiotics (2000)vol. 53, No. 12, pp. 1397-1400 "Novel Triene-⊕-lactone Antibiotics, Oxazolomycin Derivative and Its Isomer, Produced by *Streptomyces* sp. KSM-2690".  
Gräfe U. et al., Liebigs Ann. Chem. (1992) pp. 429-432 "Biogenetic studies on oxazolomycin, a metabolite of *Streptomyces albus* (Strain JA 3453)".

* cited by examiner

*Primary Examiner*—Kamal A. Saeed  
*Assistant Examiner*—Robert Havlin

(57) ABSTRACT

Polyene oxazoles of the following formula

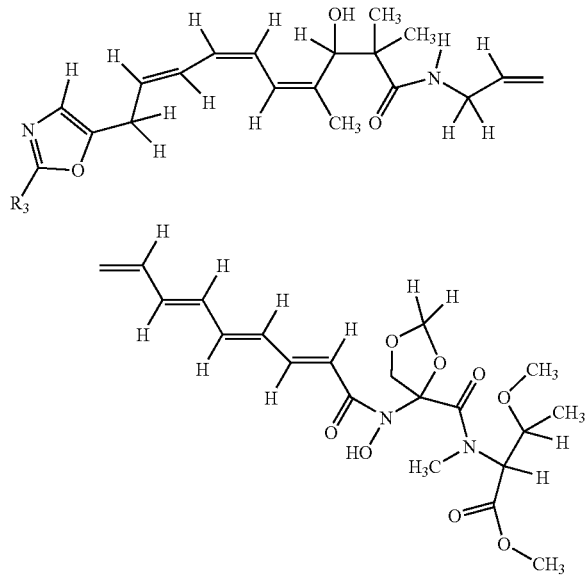

wherein $R_3$ is selected from H and methyl, are disclosed. Such compounds, and pharmaceutically acceptable salts thereof, may be used in the inhibition of tumor cell growth. The polyene oxazoles and their pharmaceutically acceptable salts may be formulated as pharmaceutical compositions with pharmaceutically acceptable carriers for use in the inhibition of tumor cells. The polyene oxazoles may be obtained from strains of *Streptomyces sparsogenes*, such as strain 022 having deposit number IDAC 270504-04.

16 Claims, 9 Drawing Sheets

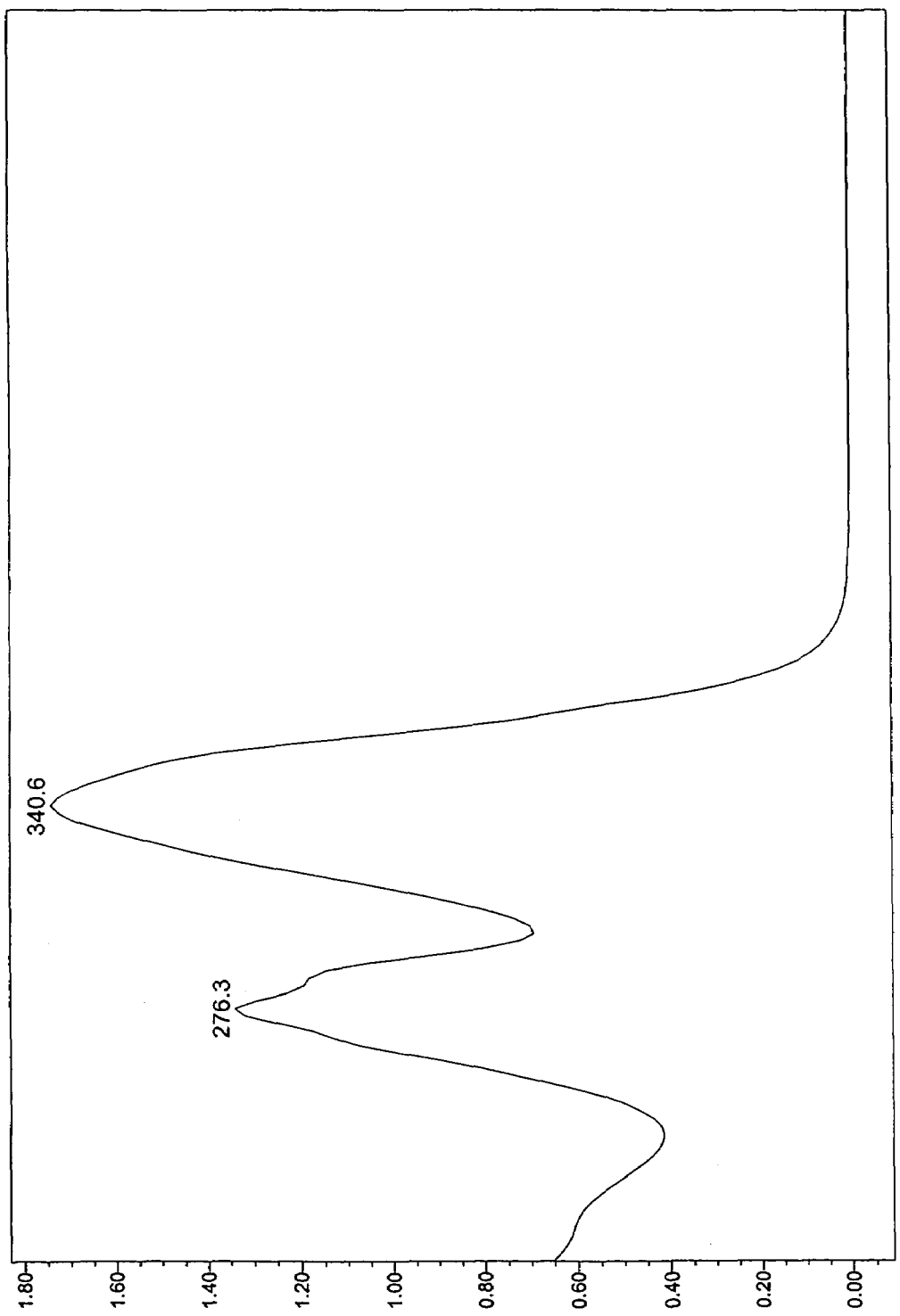

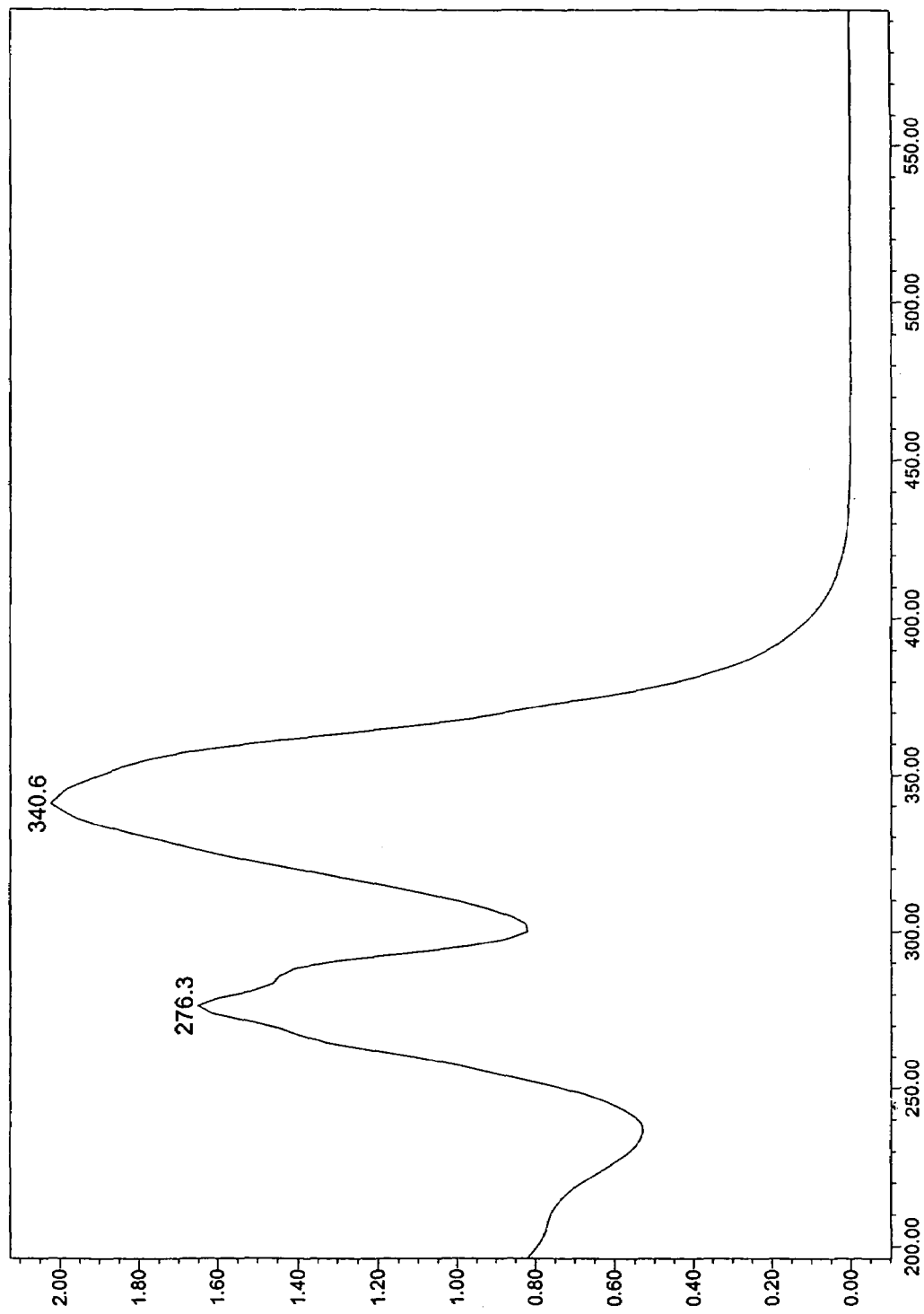

POLYENE OXAZOLES AND PROCESSES FOR THEIR PREPARATION

RELATED APPLICATIONS

This application claims priority to U.S. provisional application no. 60/477,931 filed Jun. 13, 2003, the entire contents of which are incorporated herein by reference.

FIELD OF THE INVENTION

This invention relates to novel biologically active polyene oxazoles, their pharmaceutically acceptable salts and derivatives, and to methods of obtaining them. One method for obtaining the compounds is by cultivation of *Streptomyces sparsogenes* NRRL 2940 or a mutant or variant thereof.

BACKGROUND OF THE INVENTION

Polyketides are a diverse class of naturally occurring molecules typically produced by a variety of organisms, including fungi and mycelial bacteria, in particular actinomycetes. Although polyketides have widely divergent structures, they are classified together because they all share a common biosynthetic pathway in which the carbon backbone of these molecules are assembled by sequential, stepwise addition of two carbon or substituted two carbon units referred to as ketides. Polyene polyketides comprise a chain of ketide units that have been strung together by a series of enzymatic reactions by multimodular polyketide synthase proteins.

Polyketides are usually found in their natural environment only in trace amounts. Moreover, due to their structural complexity, polyketides are notoriously difficult to synthesize chemically. Nevertheless, polyene oxazole polyketides have been shown to exhibit antibacterial and antiviral activities. Curromycin A and B have been reported to possess antibacterial activity (Ogura et al., *J. Antibiotics*, Vol. 38, No. 5, 669-673 (1985); M. Ogura et al, *Agric. Biol. Chem.*, Vol. 49, No. 6, 1909-1910 (1985). Oxazolomycins have also been reported to exhibit antibacterial, antiviral and also in some cases, antitumor activity against P388 leukemia cells (Kansaki et al., *Biosc. Biotechnol. Biochem.*, Vol. 62, No. 3, 438-442 (1998); Mori et al., *Tetrahedron Letters*, Vol. 26, No. 8, 1073-1076 (1985); Tonew et al., *Acta Virol.*, Vol. 36, 166-177 (1992)). These compounds all possess a pyroglutamate spiro β-lactone ring at one end of the molecule.

Although large numbers of therapeutically important polyketides have been identified, there remains a need to obtain novel polyketides that have enhanced properties or possess completely novel bioactivities. The complex polyketides produced by modular polyketide synthases are particularly valuable, in that they include compounds with known utility as antihelminthics, insecticides, immunosuppressants, cytotoxic, antiviral, antifungal or antibacterial agents. Because of their structural complexity, such novel polyketides are not readily obtainable by total chemical synthesis. The present invention addresses this need by providing a new class of polyene oxazole polyketide compounds with therapeutic activity.

SUMMARY OF THE INVENTION

The invention provides a polyene oxazole of compound 1 as illustrated below,

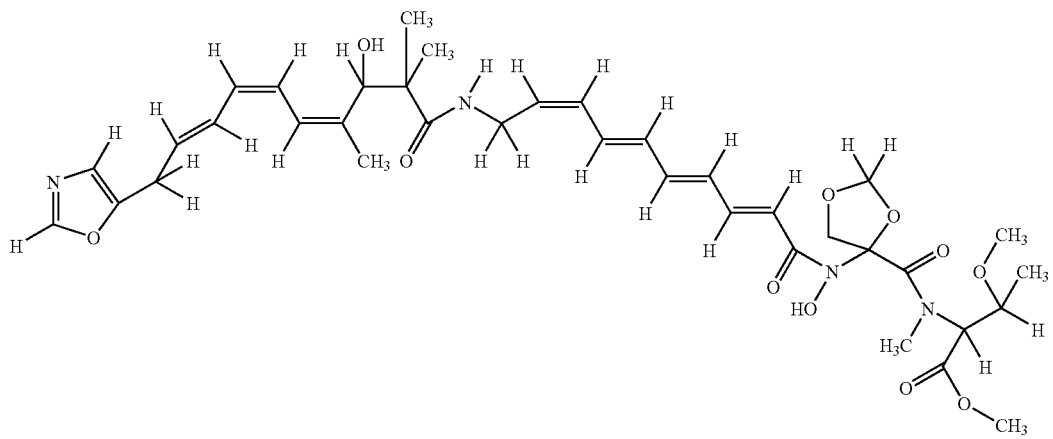

Compound 1 or a pharmaceutically acceptable salt of Compound 1.

The invention further provides a polyene oxazole of compound 2 as illustrated below,

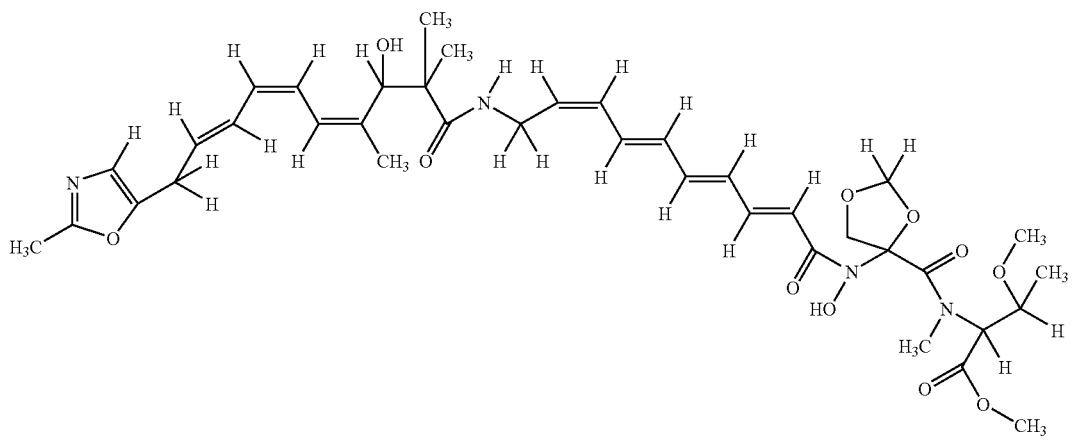

Compound 2 or a pharmaceutically acceptable salt of Compound 2.

In another aspect the invention provides polyene oxazones of Formula I, as illustrated below, which compounds may be derived by chemical modification of Compound 1 or Compound 2.

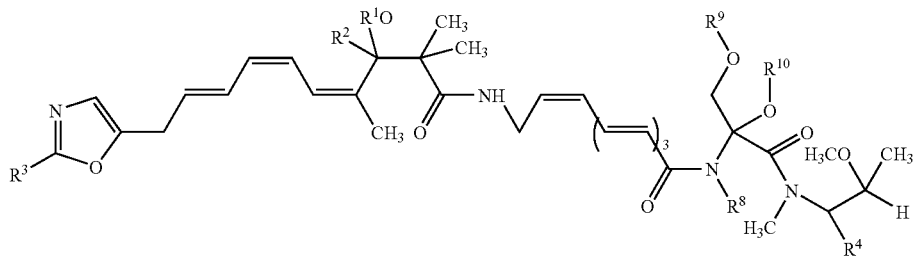

Formula I wherein, $R^1$ is selected from H, $C_{1-6}$ alkyl, $C_{2-7}$ alkenyl, $C_{6-10}$ aryl or heteroaryl, —C(O)$C_{1-6}$ alkyl, —C(O)$C_{2-7}$ alkenyl, —C(O)$C_{6-10}$ aryl or heteroaryl;

$R^2$ is a hydrogen; or $R^1$ and $R^2$ may be taken together to form a second bond between the attached oxygen and carbon atoms to form a carbonyl;

$R^3$ is selected from H or $CH_3$;

$R^4$ is selected from —COOH, —COOR$^5$, —CH$^2$OC(O)R$^6$ and —CH$_2$OR$^7$ $R^5$ and $R^6$ are selected from $C_{1-6}$ alkyl, $C_{6-10}$ aryl or arylalkyl;

$R^7$ is selected from H or $C_{1-6}$ alkyl;

$R^8$ is selected from H, OH, —OC(O)$C_{1-6}$ alkyl, —OC(O)$C_{6-10}$ aryl or —OC(O)$C_{6-16}$ arylalkyl;

$R^9$ and $R^{10}$ are each independently selected from H and $C_{1-6}$ alkyl; or $R^9$ and $R^{10}$ may be taken together with attached oxygen and carbon atoms to form a 1,3-dioxolane ring of formula:

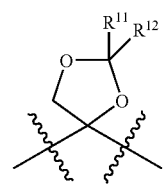

$R^{11}$ and $R^{12}$ are each independently selected from H, $C_{1-6}$ alkyl, $C_{6-10}$ aryl or $C_{6-16}$ arylalkyl;

or a pharmaceutically acceptable salt thereof.

In one embodiment, the invention provides compounds of Formula I, wherein $R^1$ is hydrogen and all other groups are as previously defined; or a pharmaceutically acceptable salt thereof.

In another embodiment, the invention provides compounds of Formula I, wherein $R^3$ is hydrogen and all other groups are as previously defined; or a pharmaceutically acceptable salt thereof.

In a further embodiment, the invention provides compounds of Formula I, wherein $R^1$ and $R^3$ are hydrogen, and all other groups are as previously defined; or a pharmaceutically acceptable salt thereof.

In a further embodiment, the invention provides compounds of Formula I, wherein $R^1$ is hydrogen and $R^3$ is methyl, and all other groups are as previously defined; or a pharmaceutically acceptable salt thereof.

In a further embodiment, the invention provides compounds of Formula I, wherein $R^1$ is $C_{1-6}$ alkyl, $C_{2-7}$ alkenyl, $C_{6-10}$ aryl or heteroaryl, and $R^3$ is methyl, and all other groups are as previously defined; or a pharmaceutically acceptable salt thereof.

In a further embodiment, the invention provides compounds of Formula I, wherein $R^1$ is $C(O)C_{1-6}$ alkyl, $C(O)C_{2-7}$ alkenyl, $C(O)C_{6-10}$ aryl or heteroaryl and $R^3$ is hydrogen, and all other groups are as previously defined; or a pharmaceutically acceptable salt thereof.

In a further embodiment, the invention provides compounds of Formula I, wherein $R^1$ is $C(O)C_{1-6}$ alkyl, $C(O)C_{2-7}$ alkenyl, $C(O)C_{6-10}$ aryl or heteroaryl and $R^3$ is methyl, and all other groups are as previously defined; or a pharmaceutically acceptable salt thereof.

The following are exemplary compounds of the invention:

Compound 1

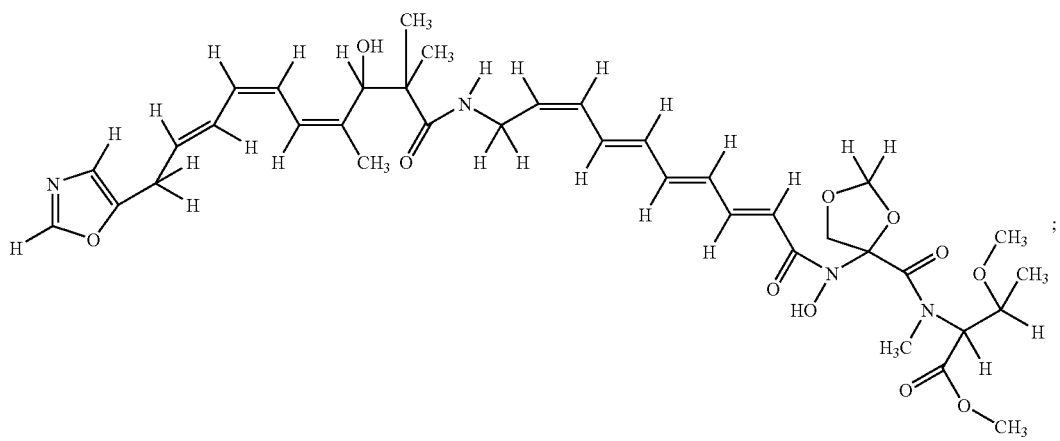

Compound 2

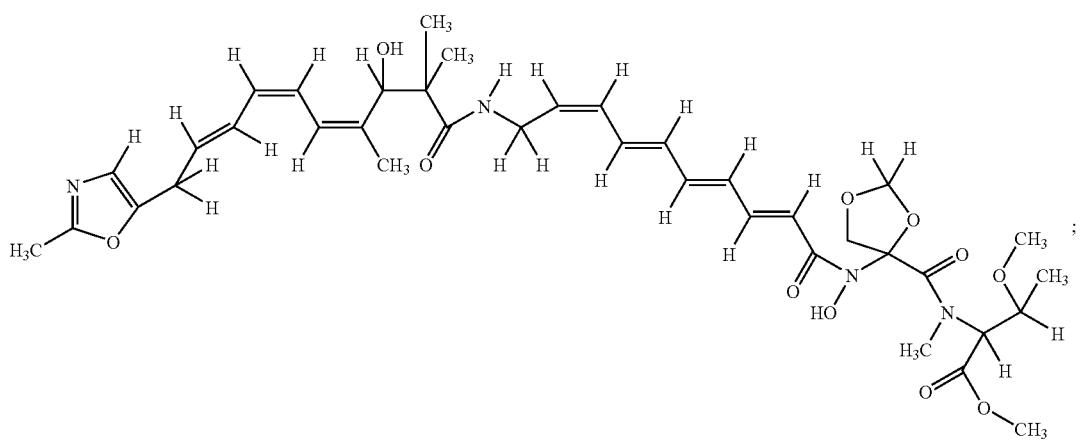

Compound 3

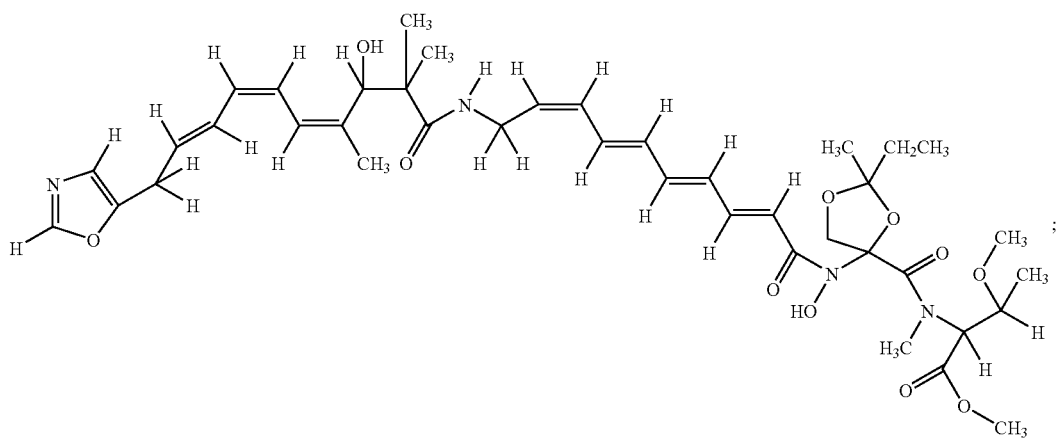

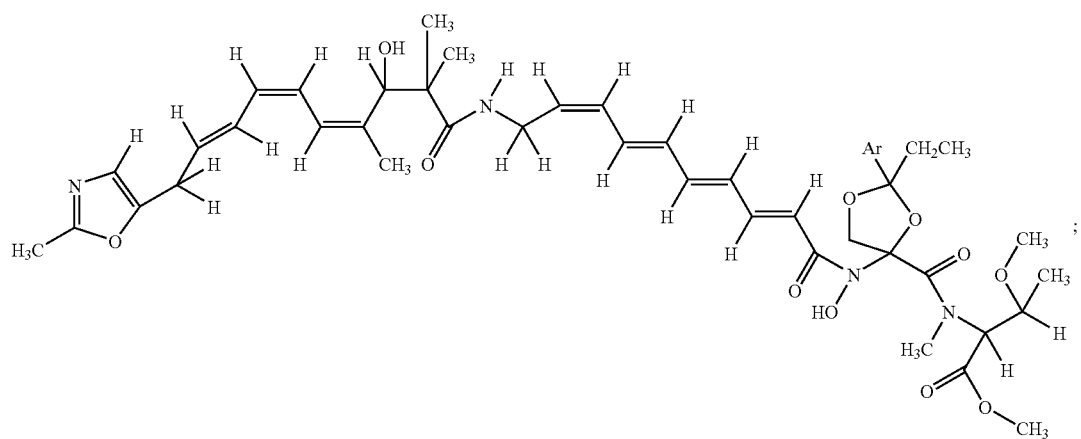
Compound 4
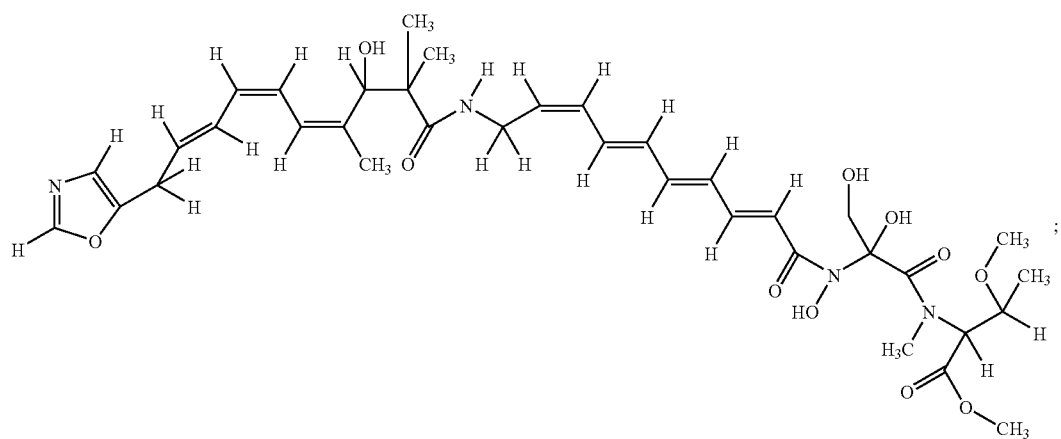
Compound 5
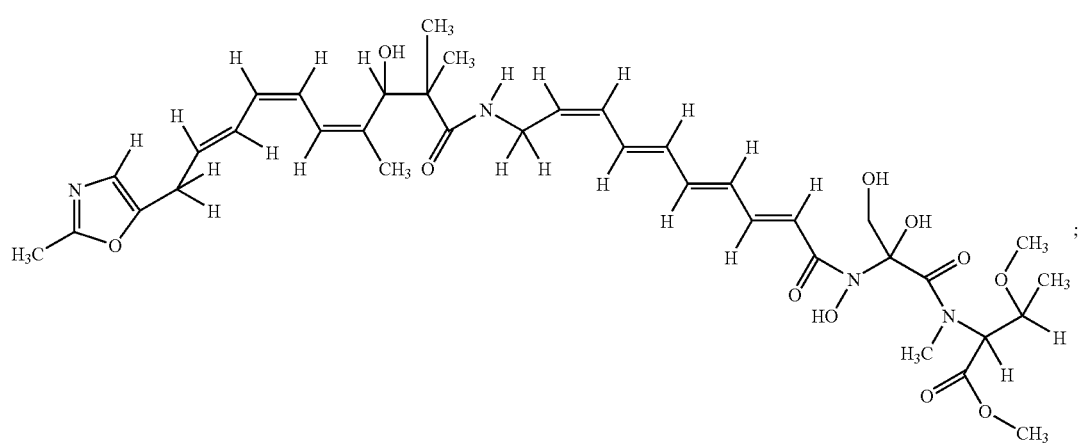
Compound 6

-continued
Compound 7
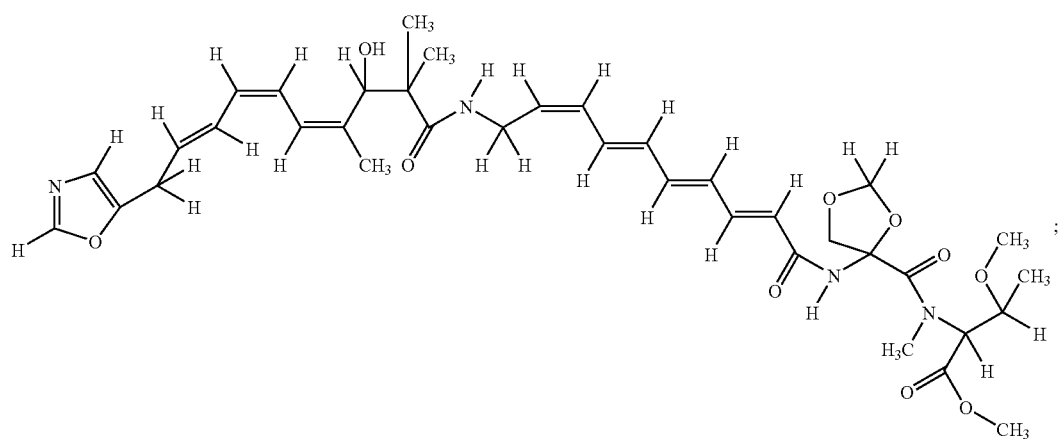
Compound 8
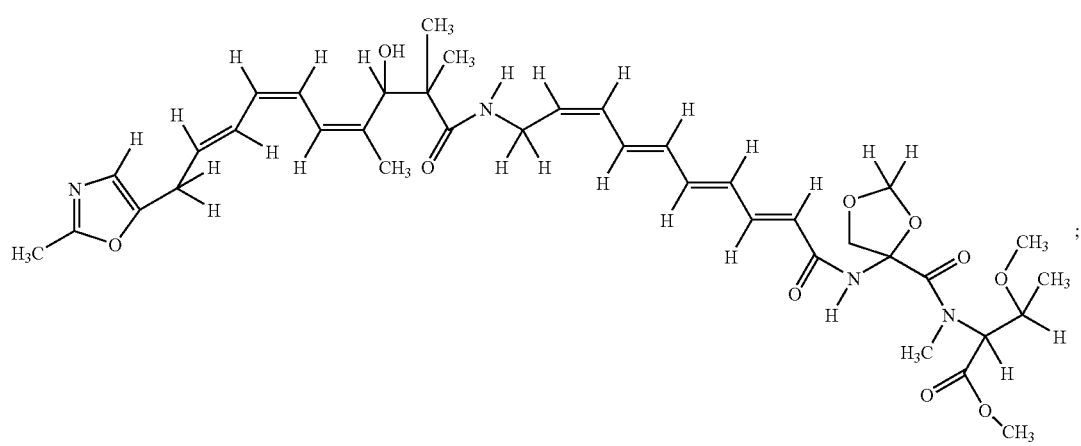
Compound 9
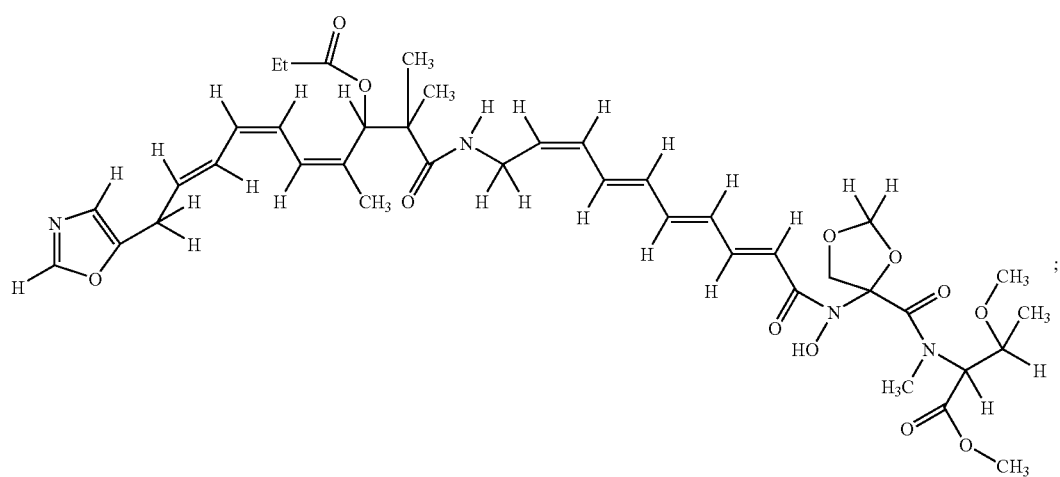

-continued
Compound 10
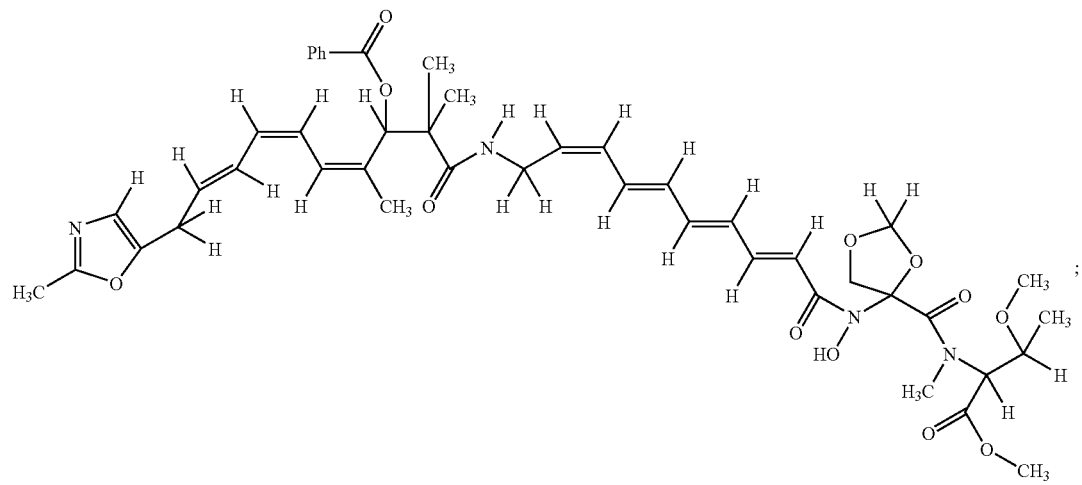
Compound 11
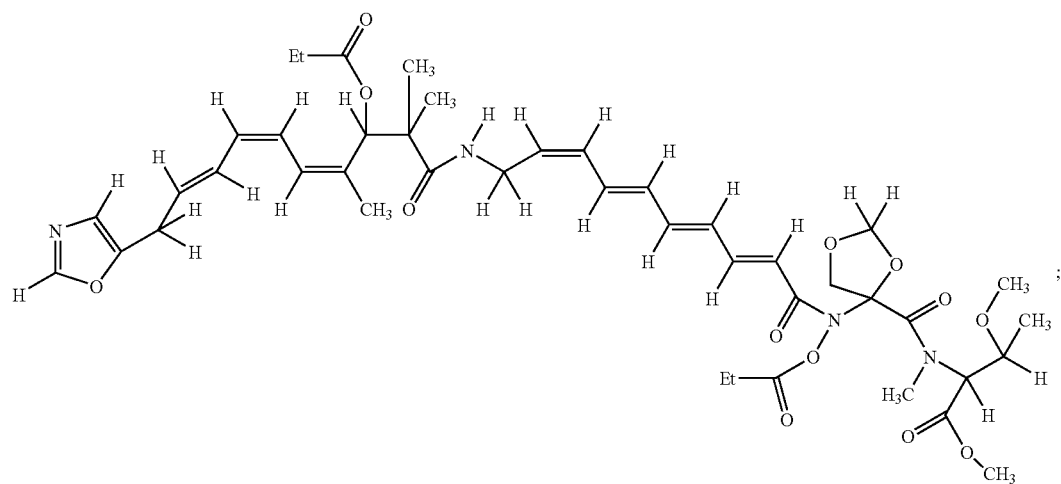
Compound 12
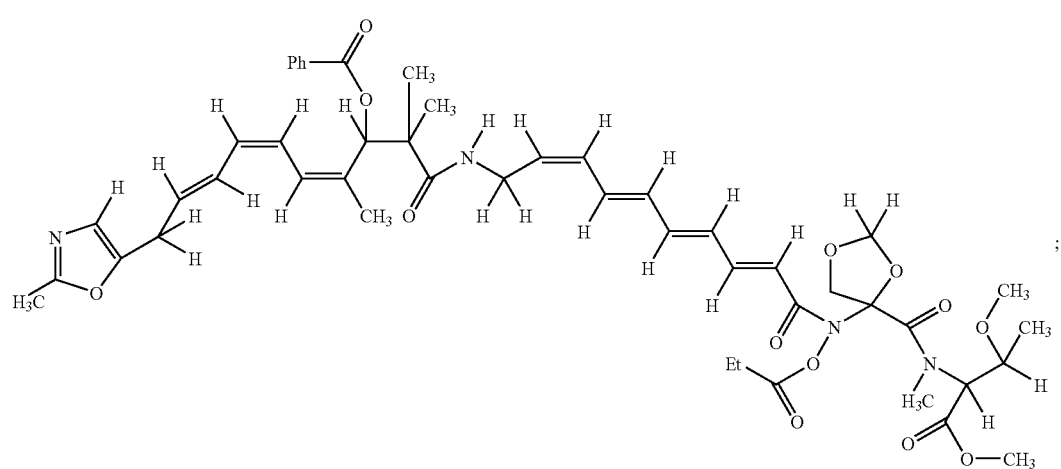

-continued
Compound 13
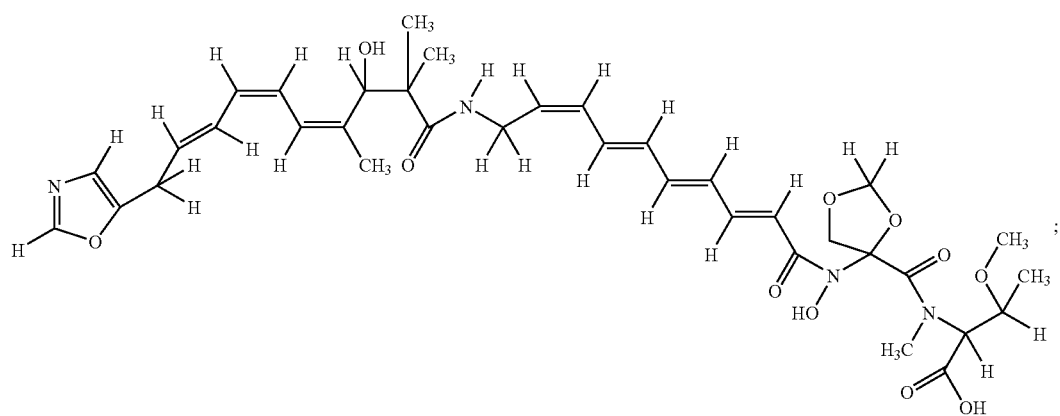
Compound 14
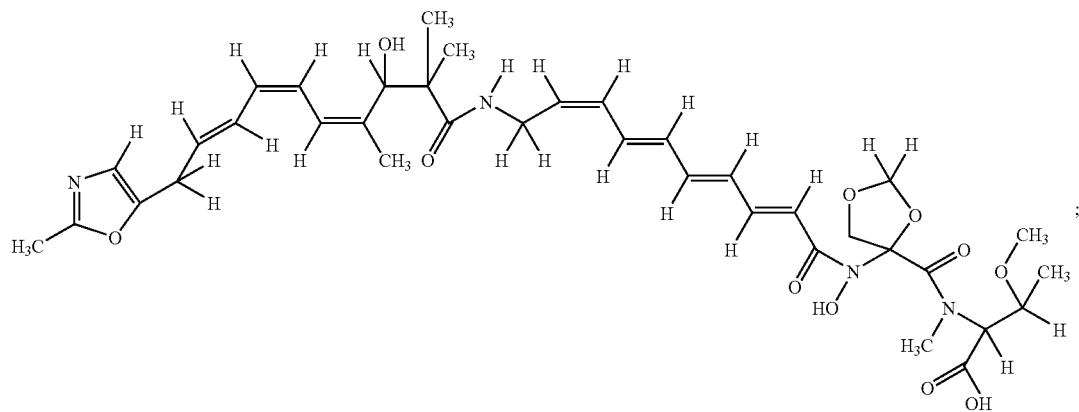
Compound 15
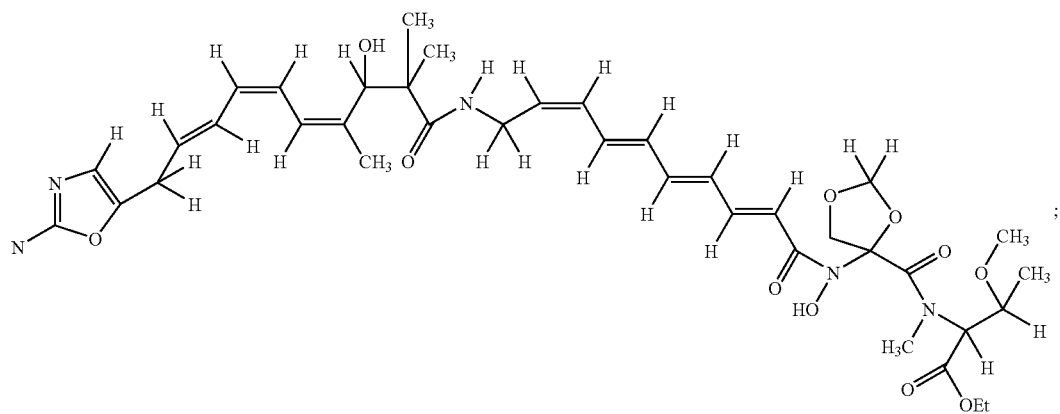

-continued
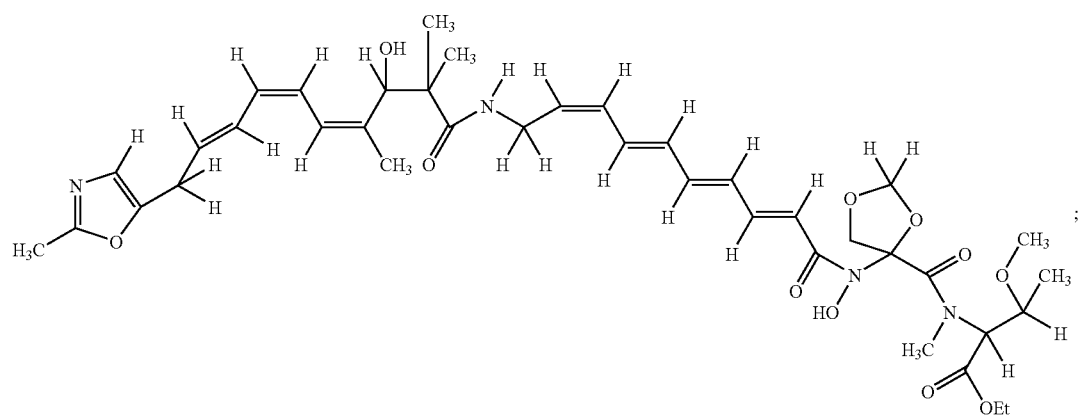
Compound 16
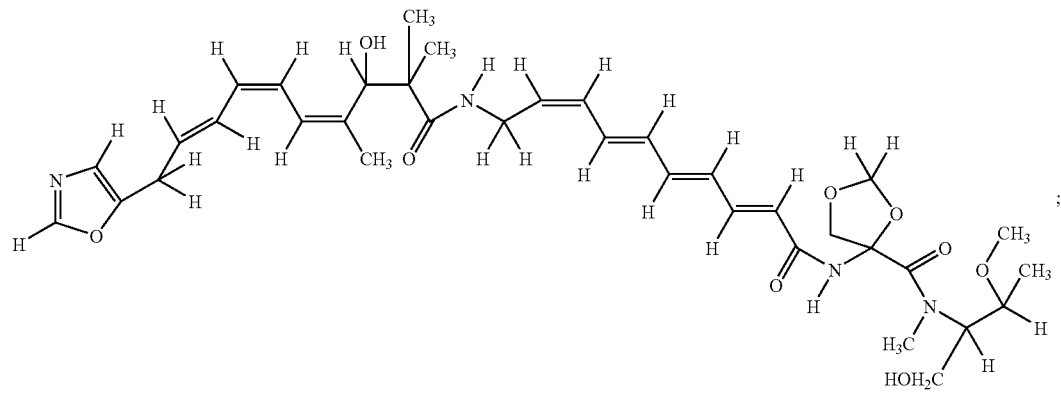
Compound 17
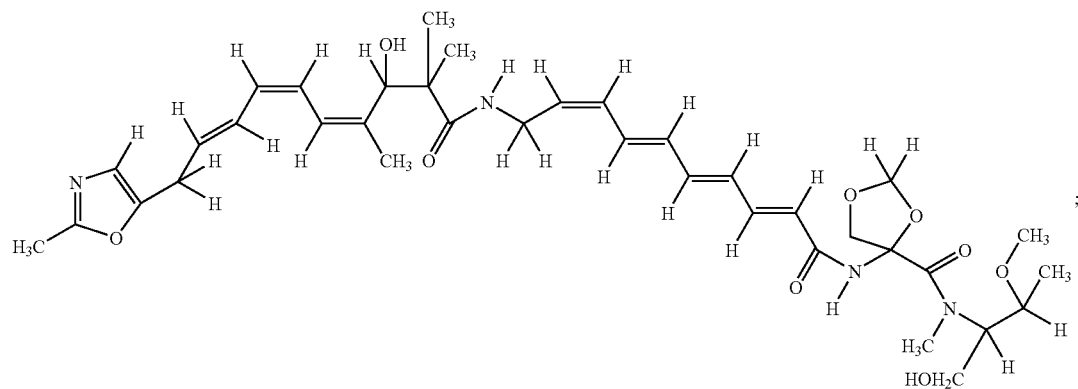
Compound 18
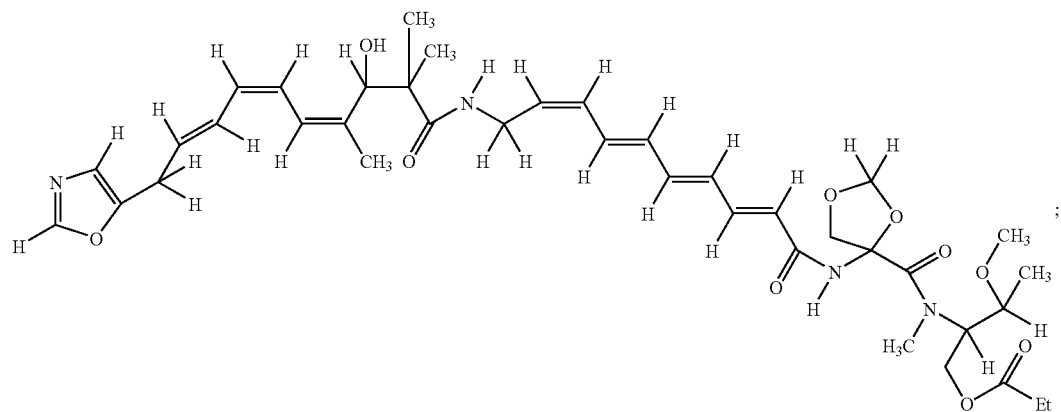
Compound 19

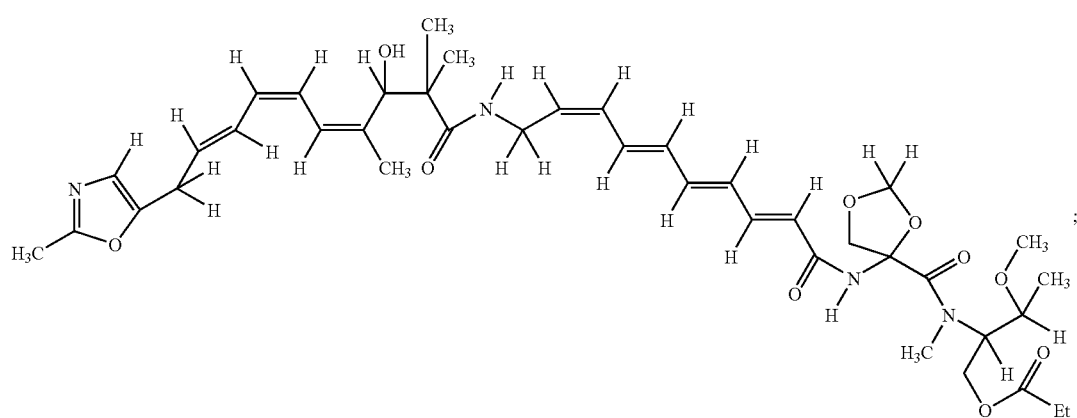
Compound 20
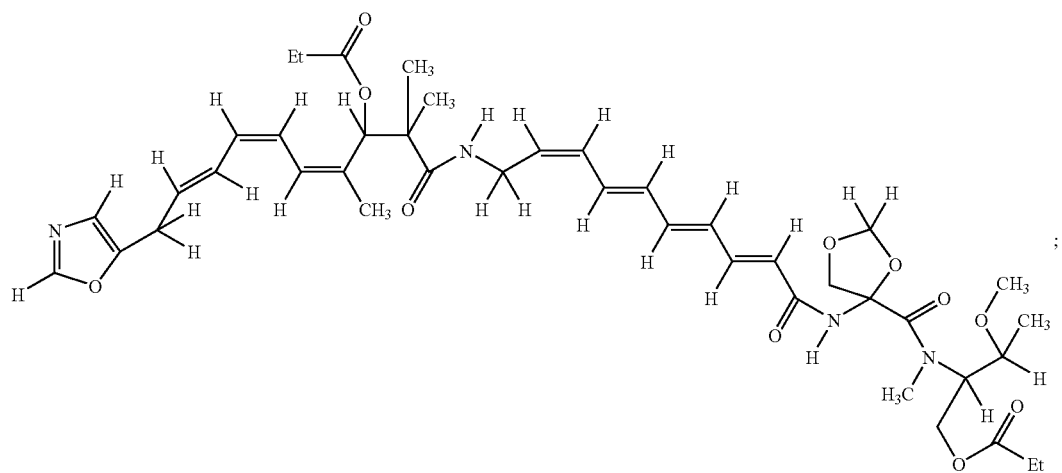
Compound 21
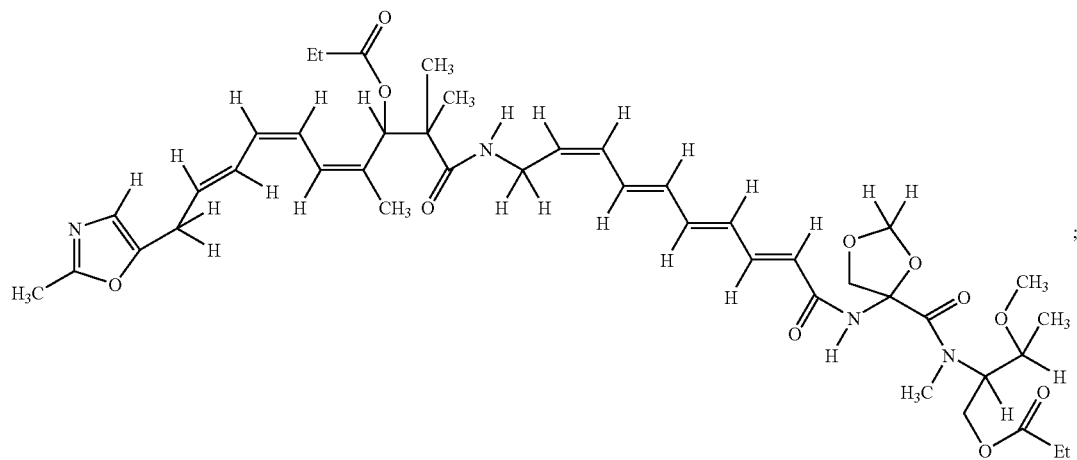
Compound 22

Compound 23
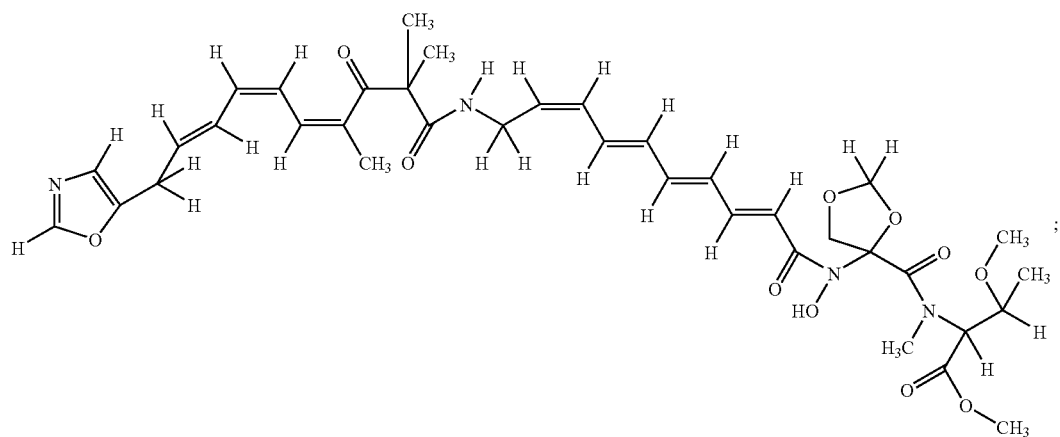
Compound 24
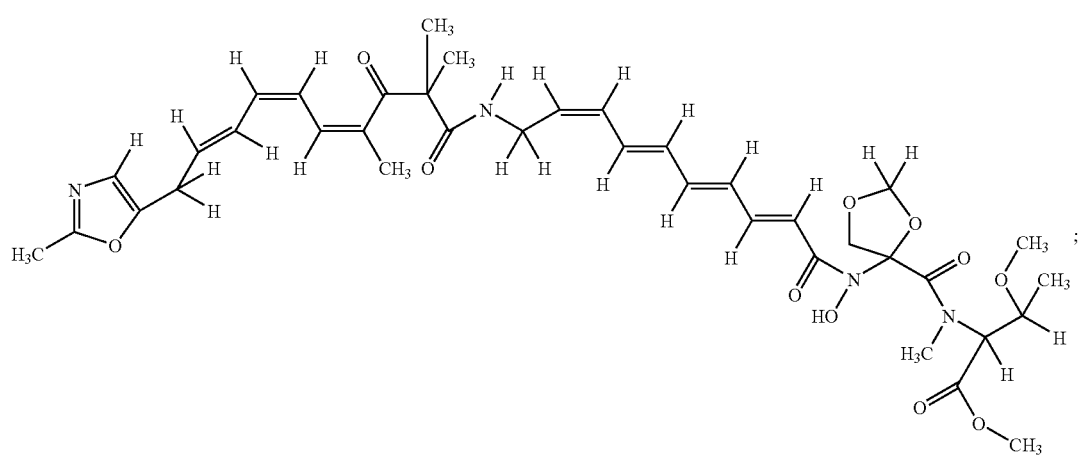
Compound 25
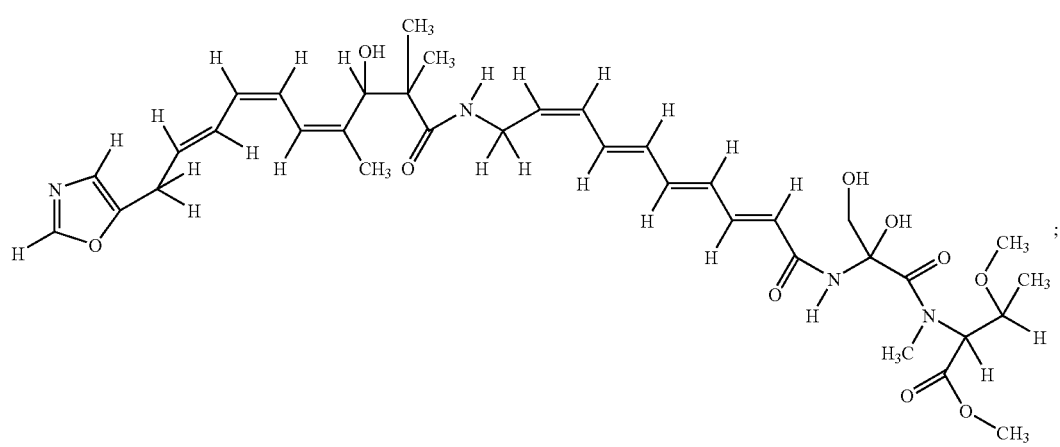

-continued

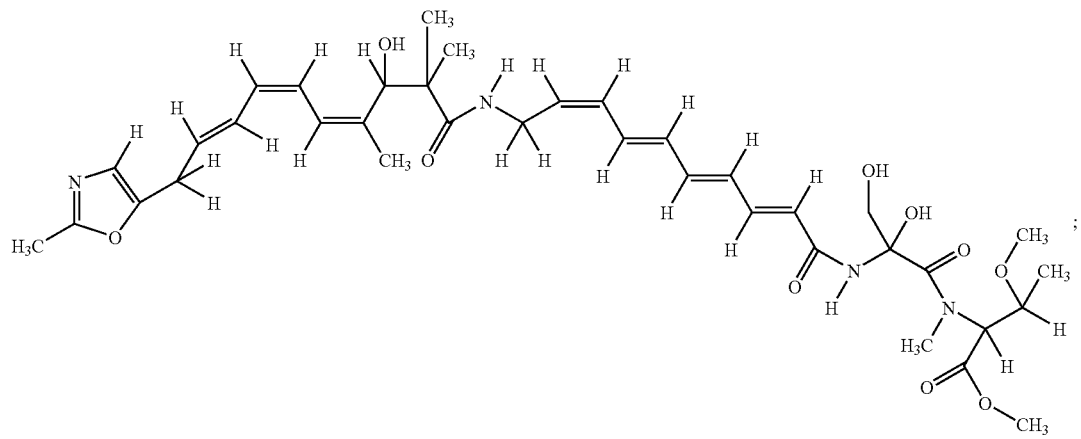

Compound 26 or a pharmaceutically acceptable salt of any one of Compounds 1-26.

The invention further relates to compositions of the compounds of Formula I together with a pharmaceutically acceptable carrier. In one embodiment, the invention relates to a pharmaceutical composition comprising a therapeutically effective amount of Compound 1, Compound 2, or a pharmaceutically acceptable salt of Compound 1 or 2, together with a pharmaceutically acceptable carrier. In another embodiment, the invention relates to a pharmaceutical composition comprising a therapeutically effective amount of at least one compound of selected from compounds 1 to 26, or a pharmaceutically acceptable salt of a compound selected from compounds 1 to 26, together with a pharmaceutically acceptable carrier.

The invention further provides a polyene oxazole obtained by a method comprising: (a) cultivating a *Streptomyces* strain under aerobic conditions in a nutrient medium comprising at least one source of carbon atoms and at least one source of nitrogen atoms, and (b) isolating a polyene oxazole from the bacteria cultivated in (a). In one embodiment, the strain is *Streptomyces sparsogenes* NRRL 2940 or a mutant thereof. In another embodiment, the strain is the *Streptomyces sparsogenes* strain deposited at the International Depositary Authority of Canada and having accession no. 270504-04. In a further embodiment, the polyene oxazole generates a $^1$H NMR spectra essentially as shown in FIGS. 3, 4 or 5. In a further embodiment, the polyene oxazole is Compound 1 or Compound 2. In a further embodiment, the nutrient medium is selected from the media of Table 1.

The invention further provides a method for producing a polyene oxazole of the invention comprising cultivation of a *Streptomyces* strain in a nutrient medium comprising at least one source of carbon atoms and at least one source of nitrogen atoms, and isolation and purification of the polyene oxazole. In another embodiment, the strain is a *Streptomyces sparsogenes*. In a further embodiment, the strain is *Streptomyces sparsogenes* NRRL 2940 or a mutant thereof. In a further embodiment, the strain is the *Streptomyces sparsogenes* strain having accession no. 270504-04 deposited at the International Depositary Authority of Canada. In a further embodiment, the carbon and nitrogen source is selected from the components of Table 1. In a further embodiment, the nutrient medium is selected from the media of Table 1. In a further embodiment, the cultivation is carried out under aerobic conditions. In a further embodiment, the cultivation is carried out at a temperature ranging from about 18° C. to about 40° C., preferably between 18° C. and 30° C. In a further embodiment, the cultivation is carried out at a pH ranging from about 6 to about 9.

The invention further provides polyene oxazoles of Formula I that are a derivative or structural analog of Compound 1 or Compound 2. In one embodiment the polyene oxazoles of Formula I are produced by post-synthesis chemical modification of Compound 1 or Compound 2.

The invention further provides the *Streptomyces sparsogenes* strain having accession no. 270504-04 deposited at the International Depositary Authority of Canada.

The invention further provides use of a compound of Formula 1 to inhibit tumor cell growth. In one embodiment, the invention provides a method of inhibiting tumor cell growth in a subject in need of such treatment, comprising administering to the subject in need an effective amount of a compound of Formula I. In another embodiment, the method comprises administering to said subject a therapeutically effective amount of Compound 1 or Compound 2. In still another embodiment, the method comprises administering to said subject a pharmaceutically acceptable salt of Compound 1 or Compound 2. In a further embodiment, the method comprises administering to said subject a pharmaceutical composition comprising either Compound 1 or Compound 2 and a pharmaceutically acceptable carrier. In a further embodiment, the invention provides use of Compound 1, Compound 2 or a compound of Formula I as a cytotoxic agent to inhibit cell growth. In a further embodiment, the invention provides use of Compound 1 or Compound 2 in the preparation of a medicament to inhibit tumor growth.

BRIEF DESCRIPTION OF THE DRAWINGS

FIGS. 1*a*, 1*b* and 1*c* are HPLC chromatogram traces of isolation of Compounds 1 and 2, wherein FIG. 1*a* is a HPLC chromatogram trace of the crude mixture, FIG. 1*b* is a HPLC chromatogram trace of pure Compound 1, and FIG. 1*c* is a HPLC chromatogram trace of pure Compound 2.

FIGS. 2*a* and 2*b* are ultraviolet spectra, wherein FIG. 2*a* is the ultraviolet spectrum for Compound 1, and FIG. 2*b* is the ultraviolet spectrum for Compound 2.

DETAILED DESCRIPTION

Figure 1A:
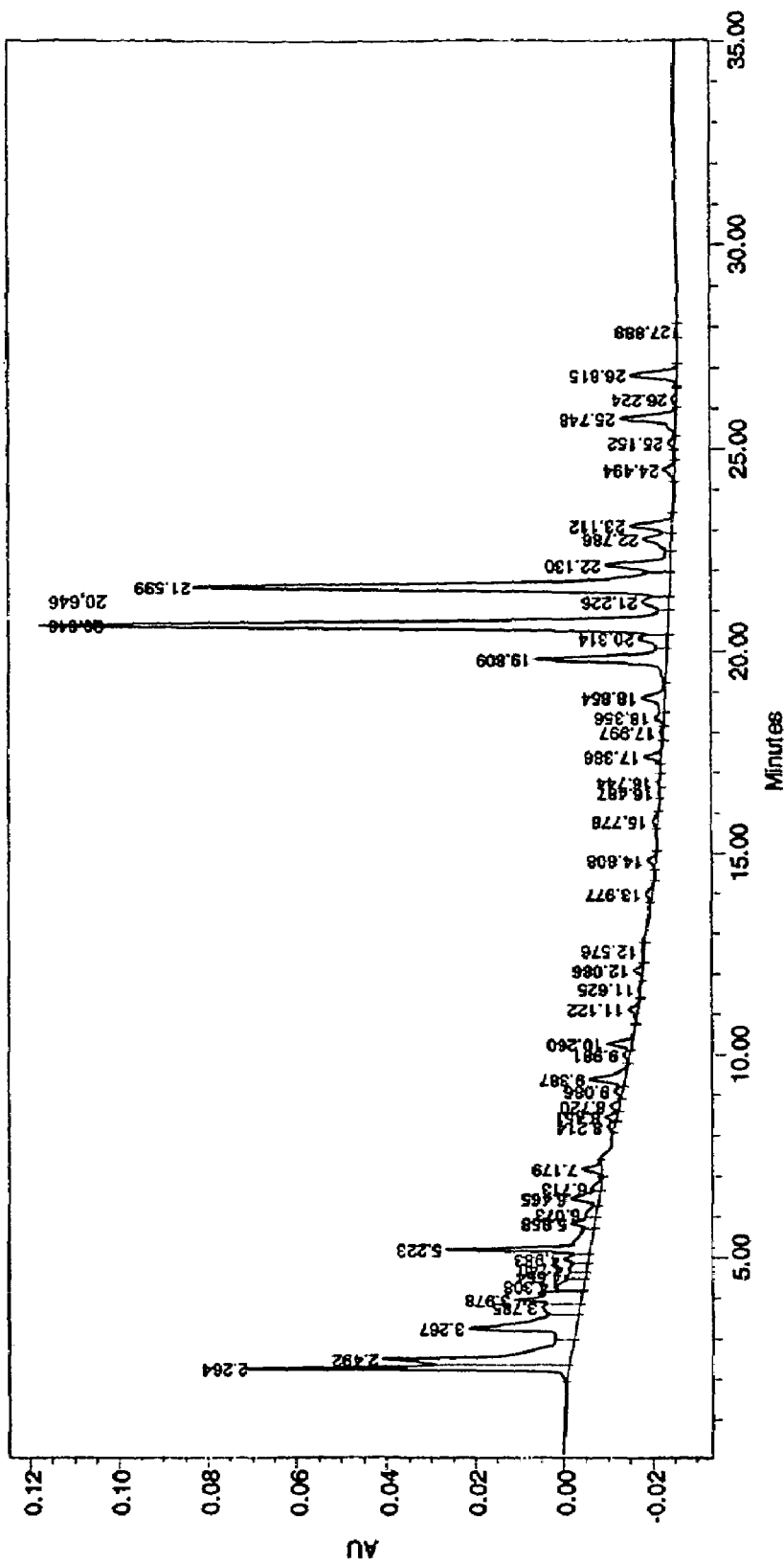

The present invention relates to novel polyene oxazoles, exemplified herein as Compound 1 and Compound 2, which are isolated from strains of actinomycetes, *Streptomyces* sp. such as *Streptomyces sparsogenes* NRRL 2940, or a mutant or a variant thereof.

The invention further relates to pharmaceutically acceptable salts and derivatives of Compound 1 and Compound 2, and to methods for obtaining such compounds. One method of obtaining the compounds is by cultivating *Streptomyces sparsogenes* NRRL 2940, or a mutant or a variant thereof, under suitable *Streptomyces* sp. culture conditions preferably using the fermentation protocol described hereinbelow.

The invention also relates to polyene oxazoles of Formula I produced from Compound 1 or Compound 2 by selective chemical modification of Compound 1 or Compound 2 using techniques described herein and well known to those skilled in the synthesis of natural products.

The present invention also relates to pharmaceutical compositions comprising a polyene oxazole selected from Compound 1, Compound 2, pharmaceutically acceptable salts of Compound 1 or 2, and derivatives of Compound 1 or 2 as defined by Formula I. In an aspect of this invention Compound 1 and Compound 2 are each useful as a cytotoxic agent, and for use as inhibitors of cancer cell growth. Accordingly, in an aspect the present invention relates to pharmaceutical compositions comprising Compound 1 or Compound 2 of the invention together with a pharmaceutically acceptable carrier and methods of using the compositions as a cytotoxic agent to inhibit cell growth.

I. Definitions

Certain terms, when used in this application, have their common meaning unless otherwise specified. For convenience, the meaning of some terms and phrases used in the specification, examples, and appended claims, are provided below.

The term alkyl refers to linear, branched or cyclic hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexymethyl, and the like. Alkyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino and formyl.

The term alkenyl refers to linear, branched or cyclic hydrocarbon groups containing at least one carbon-carbon double bond. Examples of alkenyl groups include, without limitation, vinyl, 1-propene-2-yl, 1-butene-4-yl, 2-butene-4-yl, 1-pentene-5-yl and the like. Alkenyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration.

The term cycloalkyl or cycloalkyl ring refers to a saturated or partially unsaturated carbocyclic ring in a single or fused carbocyclic ring system having from three to fifteen ring members. Examples of cycloalkyl groups include, without limitation, cyclopropyl, cyclobutyl, cyclopentyl, cyclohexyl, and cycloheptyl. Cycloalkyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term heterocyclyl, heterocyclic or heterocyclyl ring refers to a saturated or partially unsaturated ring containing one to four hetero atoms or hetero groups selected from O, N, NH, NR$^x$, PO$_2$, S, SO or SO$_2$ in a single or fused heterocyclic ring system having from three to fifteen ring members. Examples of a heterocyclyl, heterocyclic or heterocyclyl ring include, without limitation, morpholinyl, piperidinyl, and pyrrolidinyl. Heterocyclyl, heterocyclic or heterocyclyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term halo refers to bromine, chlorine, fluorine or iodine substituents.

The term aryl or aryl ring refers to aromatic groups in a single or fused ring system, having from five to fifteen ring members. Examples of aryl include, without limitation, phenyl, naphthyl, biphenyl, terphenyl. Aryl may optionally be substituted with one or more substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term heteroaryl or heteroaryl ring refers to aromatic groups in a single or fused ring system, having from five to fifteen ring members and containing at least one hetero atom such as O, N, S, or at least one heteroatom group such as SO or SO$_2$. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Heteroaryl groups may optionally be substituted with one or more substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl.

The compounds of the present invention can possess one or more asymetric carbon atoms and can exist as optical isomers forming mixtures of racemic or non-racemic compounds. The compounds of the present invention are useful as a single isomer or as a mixture of stereochemical isomeric forms. Diastereoisomers, i.e., nonsuperimposable stereochemical isomers, can be seperated by conventional means such as chromatography, distillation, crystallization or sublimation. The optical isomers can be obtained by resolution of the racemic mixtures according to conventional processes.

The invention encompasses isolated or purified compounds. An "isolated" or "purified" compound refers to a compound which represents at least 10%, 20%, 50%, 80% or 90% of the compound of the present invention present in a mixture, provided that the mixture comprising the compound of the invention has demonstrable (i.e. statistically significant) biological activity such as cytotoxic activity when tested in conventional biological assays known to a person skilled in the art.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a compound of the invention and a pharmaceutically acceptable carrier. As used herein, "pharmacologically effective amount," "therapeutically effective amount" or simply "effective amount" refers to that amount of polyene oxazole effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminium, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in *Journal of Pharmaceutical Sciences* (1977) 66:2. All of these salts may be prepared by conventional means from a polyketide compound of the present invention by treating the compound with the appropriate acid or base.

Unless otherwise indicated, all numbers expressing quantities of ingredients and properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set forth in the examples, tables and figures are reported as precisely as possible. Any numerical values may inherently contain certain errors resulting from variations in experiments, testing measurements, statistical analysis and such.

II. Compounds of the Invention

In one aspect of this embodiment the invention relates to a novel polyene oxazole, referred to herein as Compound 1:

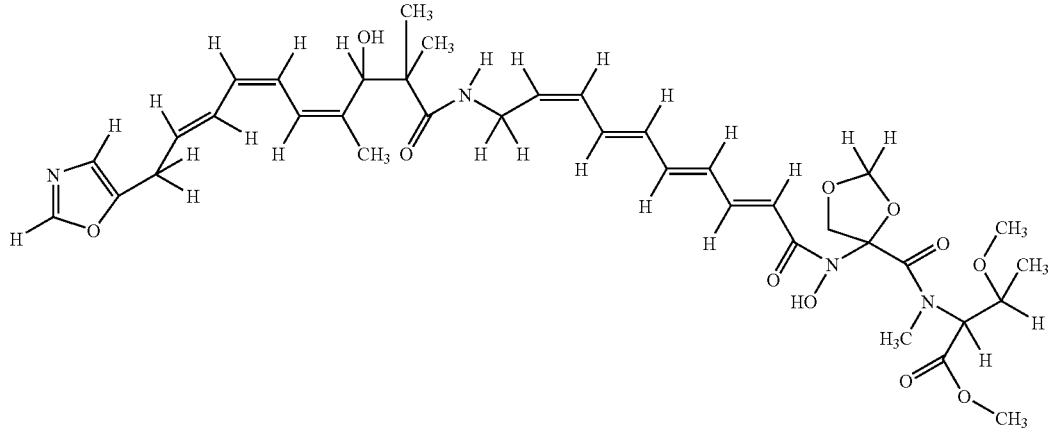

Compound 1 or, Compound 2:

Compound 2

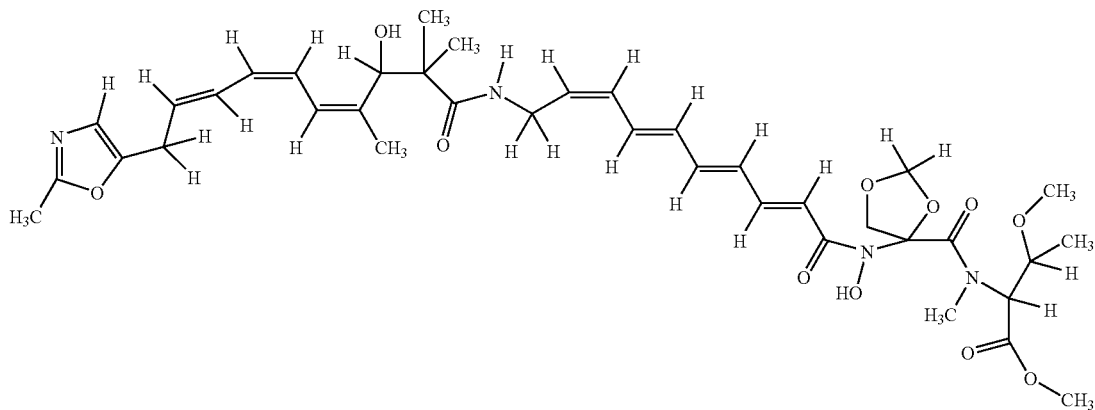

or, to a pharmaceutically acceptable salt of Compound 1 or Compound 2. Compounds 1 and 2 may be characterized by any one or more of its physicochemical and spectral properties given below, such as its mass, UV, and NMR spectroscopic data.

In another aspect the invention relates to derivatives of Compound 1 or Compound 2, as represented by the polyene oxazoles of Formula I:

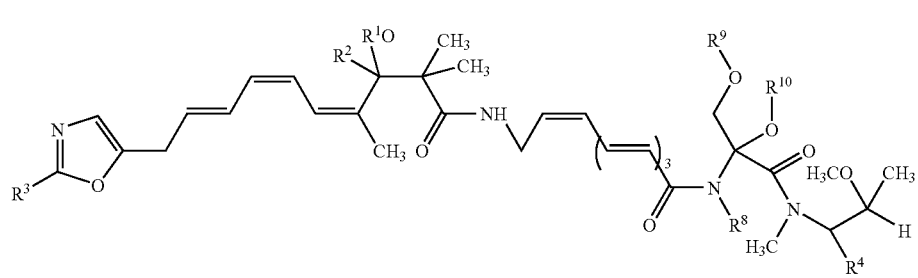

Formula I wherein, $R^1$ is selected from H, $C_{1-6}$ alkyl, $C_{2-7}$ alkenyl, $C_{6-10}$ aryl or heteroaryl, —C(O)$C_{1-6}$ alkyl, —C(O)$C_{2-7}$ alkenyl, —C(O)$C_{6-10}$ aryl or heteroaryl;

$R^2$ is a hydrogen; or $R^1$ and $R^2$ may be taken together to form a second bond between the attached oxygen and carbon atoms to form a carbonyl;

$R^3$ is selected from H or $CH_3$;

$R^4$ is selected from —COOH, —COOR$^5$, —CH$^2$OC(O)R$^6$ and —CH$_2$OR$^7$ $R^5$ and $R^6$ are selected from $C_{1-6}$ alkyl, $C_{6-10}$ aryl or arylalkyl;

$R^7$ is selected from H or $C_{-6}$ alkyl;

$R^8$ is selected from H, OH, —OC(O)$C_{1-6}$ alkyl, —OC(O)$C_{6-10}$ aryl or —OC(O)$C_{6-16}$ arylalkyl;

$R^9$ and $R^{10}$ are each independently selected from H and $C_{1-6}$ alkyl; or $R^9$ and $R^{10}$ may be taken together with attached oxygen and carbon atoms to form a 1,3-dioxolane ring of formula:

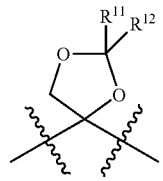

$R^{11}$ and $R^{12}$ are each independently selected from H, $C_{1-6}$ alkyl, $C_{6-10}$ aryl or $C_{6-16}$ arylalkyl;

or a pharmaceutically acceptable salt thereof.

In a further embodiment the invention provides compounds of Formula I, wherein $R^1$ is hydrogen and all other groups are as previously defined; or a pharmaceutically acceptable salt thereof.

In a further embodiment the invention provides compounds of Formula I, wherein $R^3$ is hydrogen and all other groups are as previously defined; or a pharmaceutically acceptable salt thereof.

In a further embodiment the invention provides compounds of Formula I, wherein $R^1$ and $R^3$ are hydrogens, and all other groups are as previously defined; or a pharmaceutically acceptable salt thereof.

In a further embodiment the invention provides compounds of Formula I, wherein $R^1$ is hydrogen and $R^3$ is methyl, and all other groups are as previously defined; or a pharmaceutically acceptable salt thereof.

In a further embodiment the invention provides compounds of Formula I, wherein $R^1$ is $C_{1-6}$ alkyl, $C_{2-7}$ alkenyl, $C_{6-10}$ aryl or heteroaryl, and $R^3$ is methyl, and all other groups are as previously defined; or a pharmaceutically acceptable salt thereof.

In a further embodiment the invention provides compounds of Formula I, wherein $R^1$ is $C(O)C_{1-6}$ alkyl, $C(O)C_{2-7}$ alkenyl, $C(O)C_{6-10}$ aryl or heteroaryl and $R^3$ is hydrogen, and all other groups are as previously defined; or a pharmaceutically acceptable salt thereof.

In a further embodiment the invention provides compounds of Formula I, wherein $R^1$ is $C(O)C_{1-6}$ alkyl, $C(O)C_{2-7}$ alkenyl, $C(O)C_{6-10}$ aryl or heteroaryl and $R^3$ is methyl, and all other groups are as previously defined; or a pharmaceutically acceptable salt thereof.

The following are exemplary compounds of the invention:

Compound 1

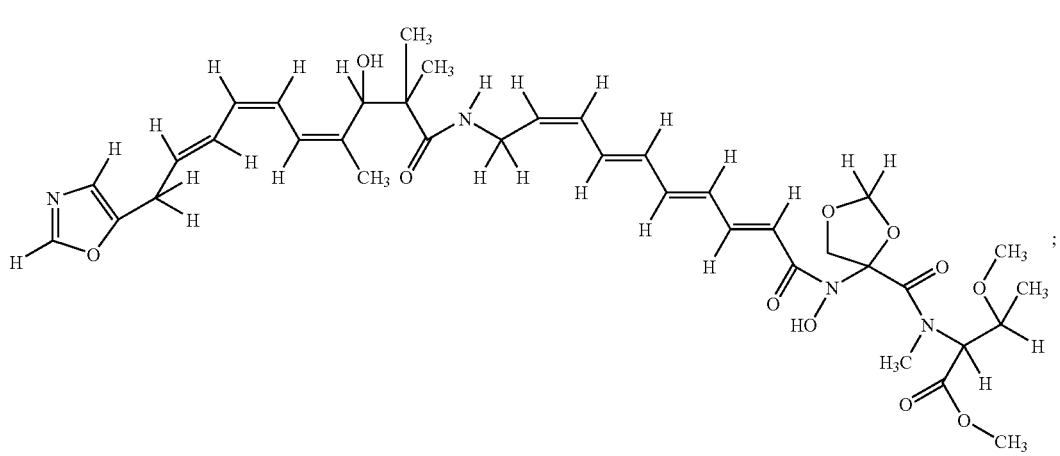

Compound 2

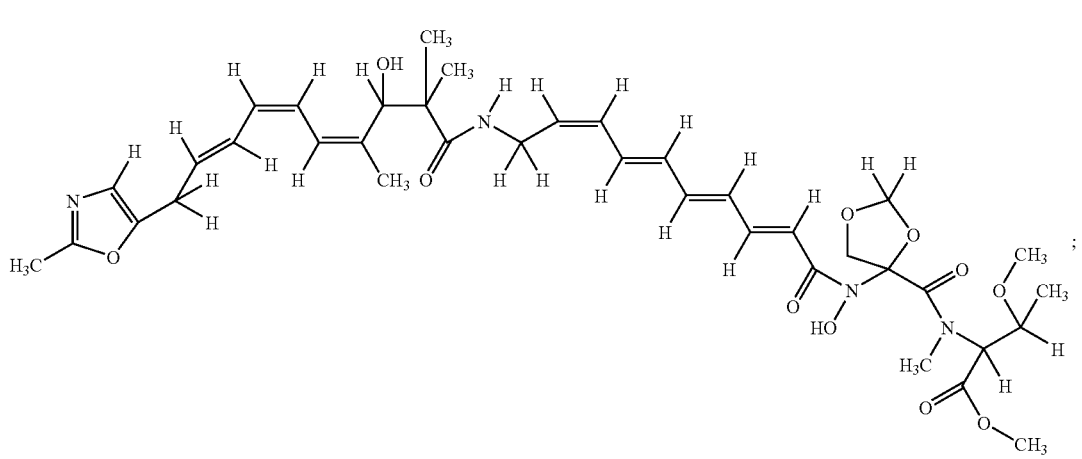

Compound 3

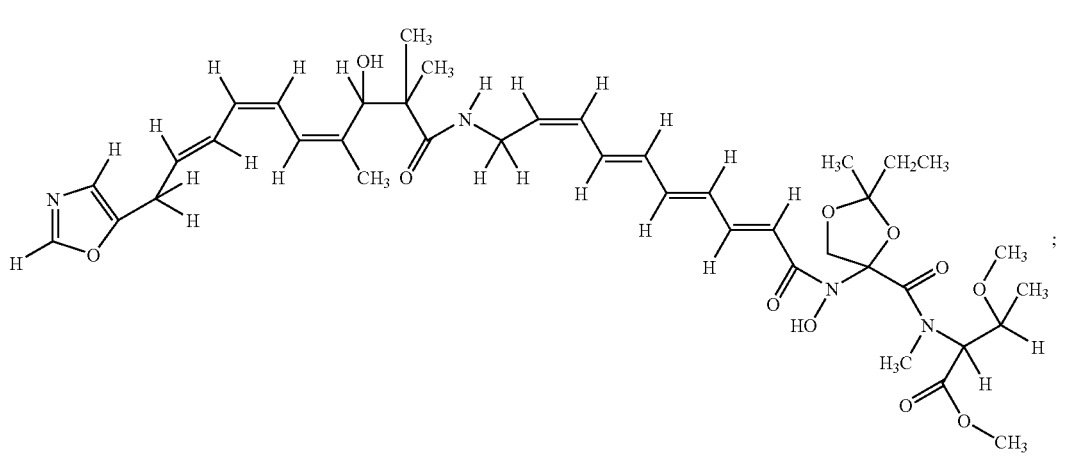

-continued
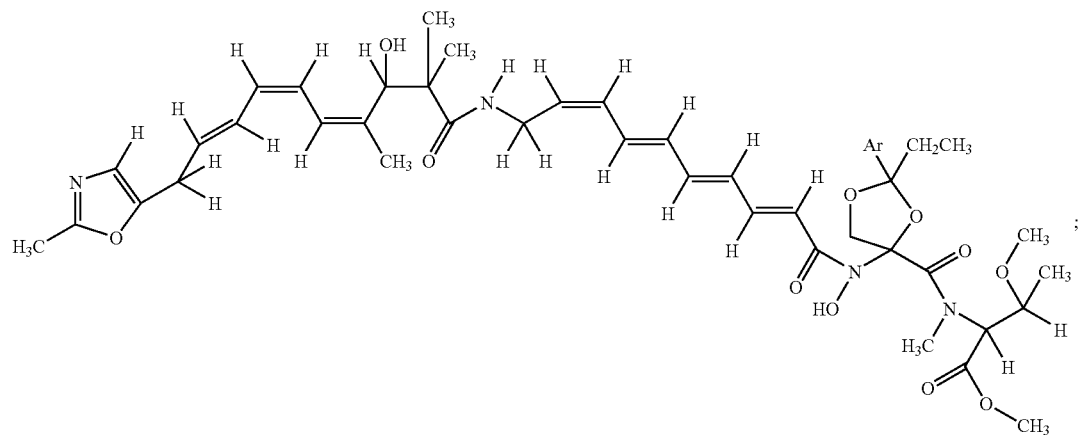
Compound 4
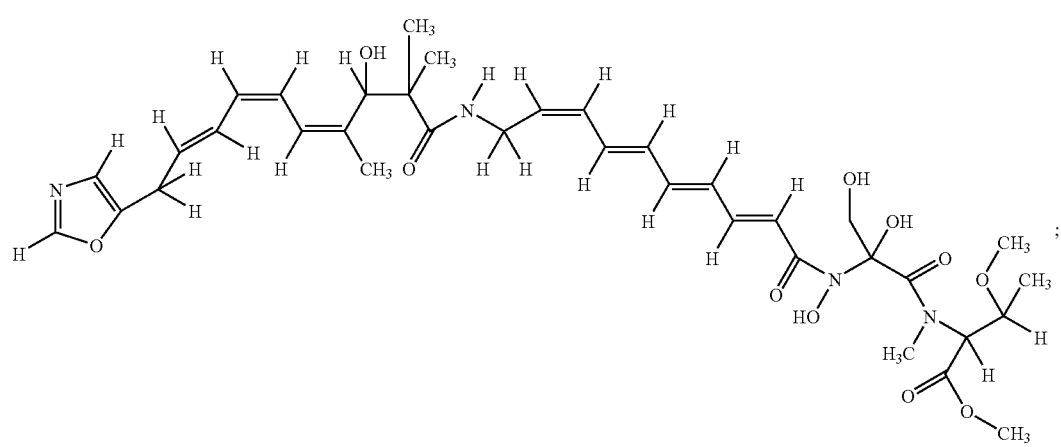
Compound 5
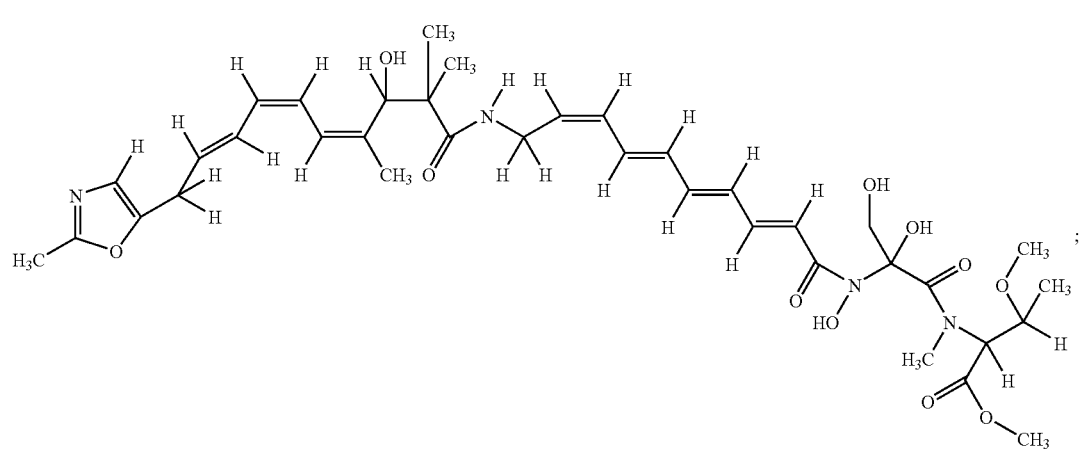
Compound 6

-continued
Compound 7
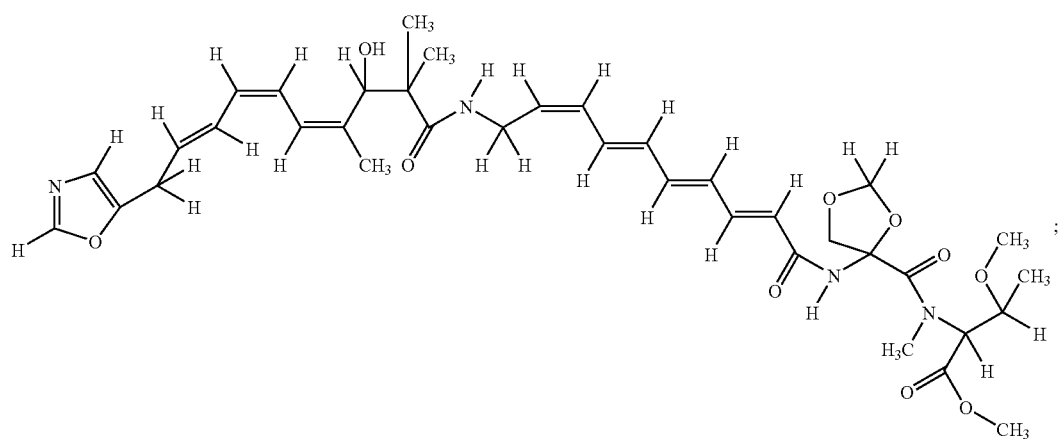
Compound 8
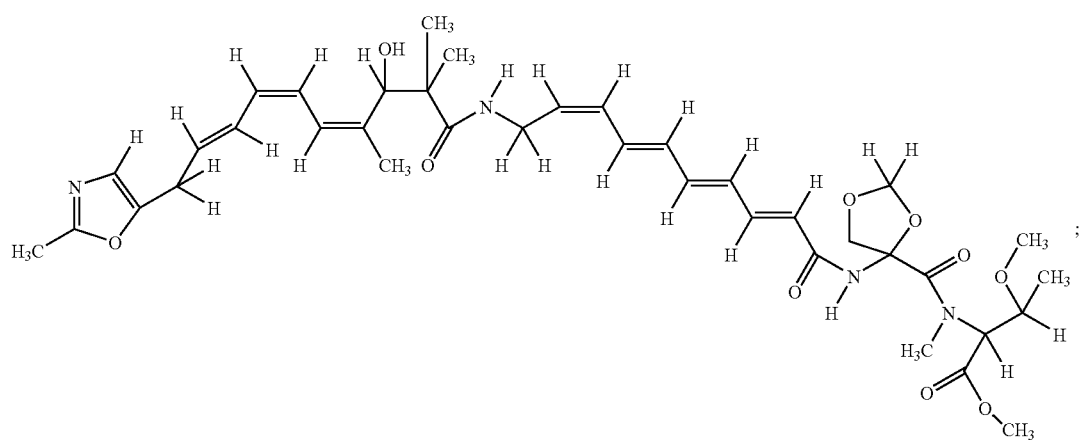
Compound 9
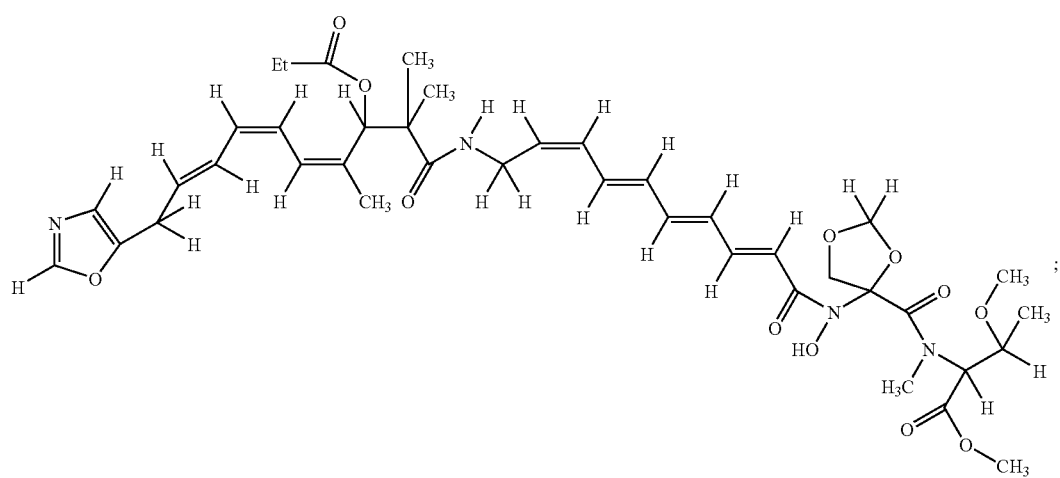

-continued
Compound 10
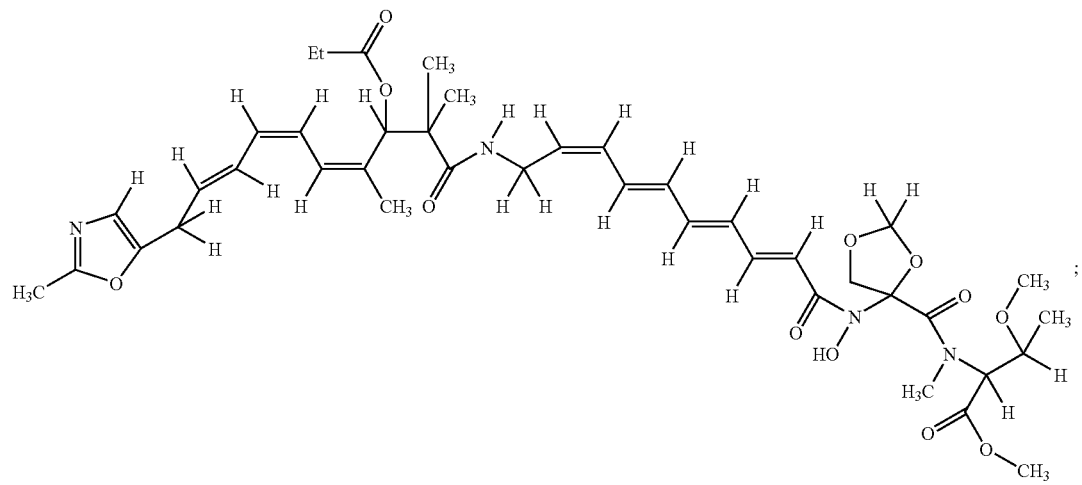
Compound 11
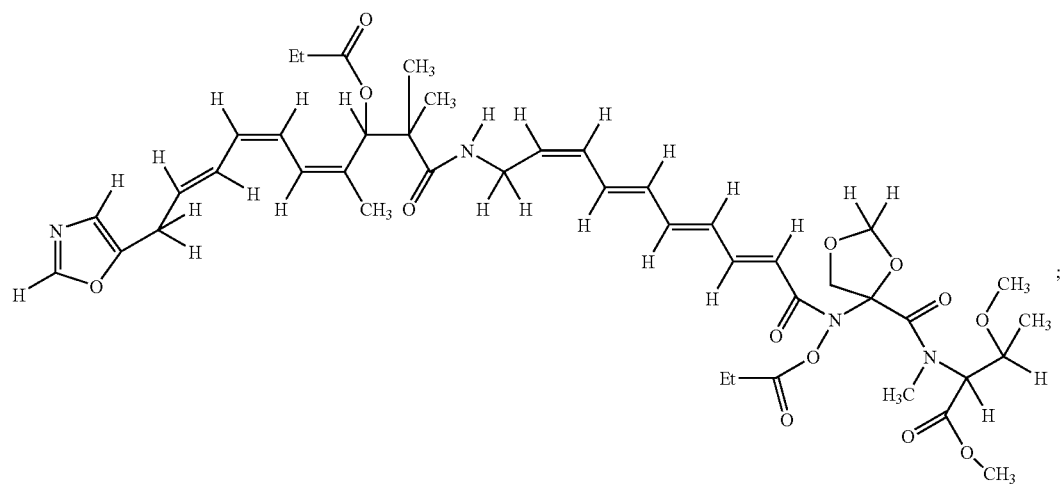
Compound 12
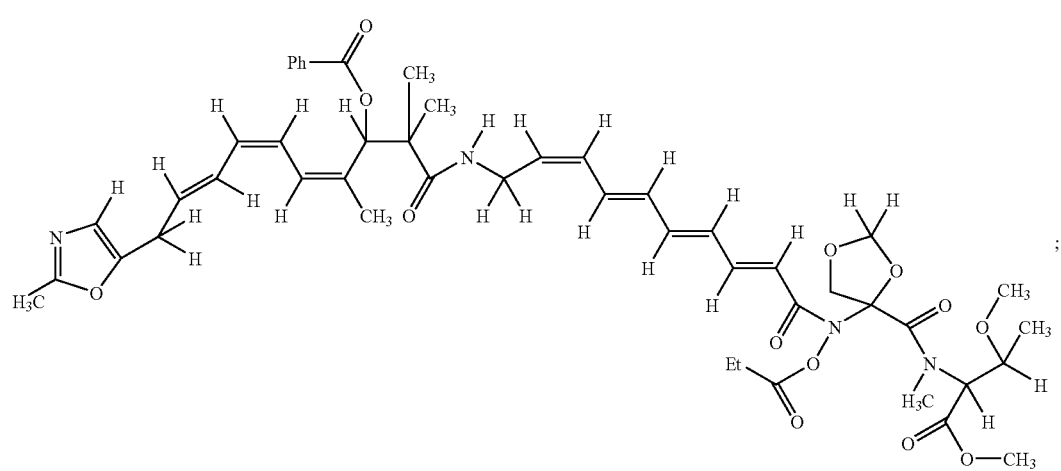

-continued
Compound 13
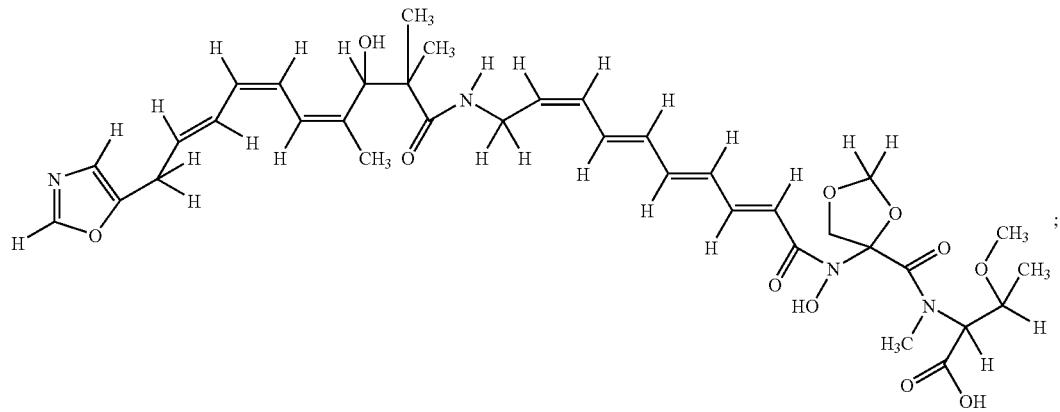
Compound 14
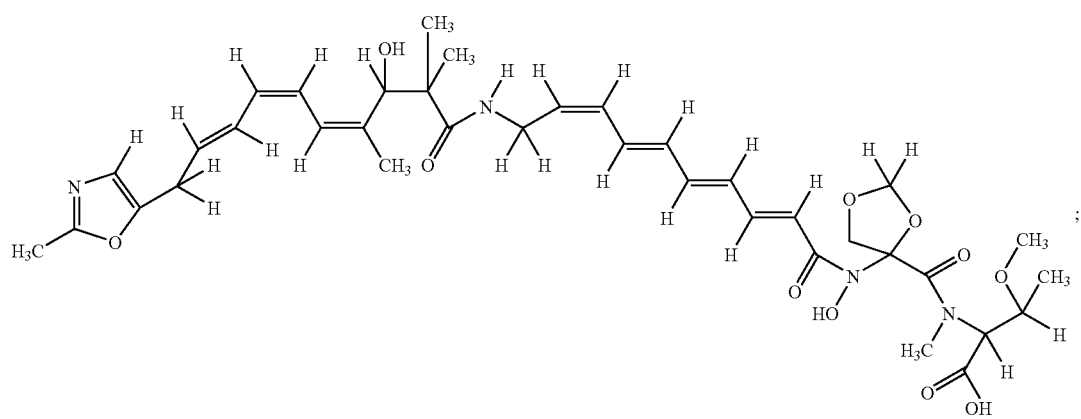
Compound 15
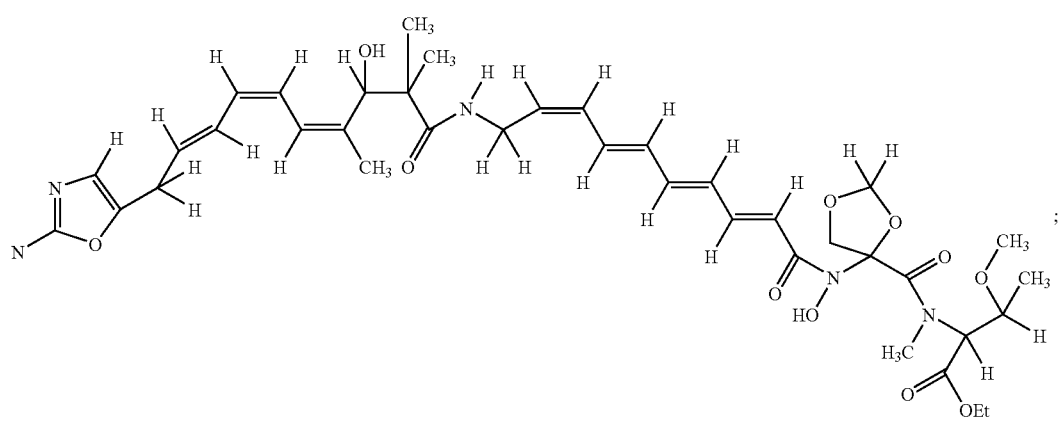
Compound 16
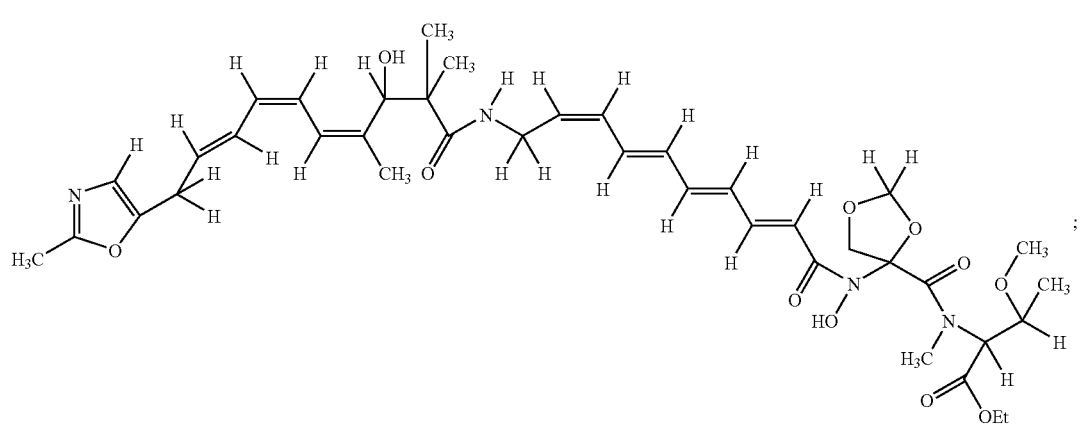

-continued
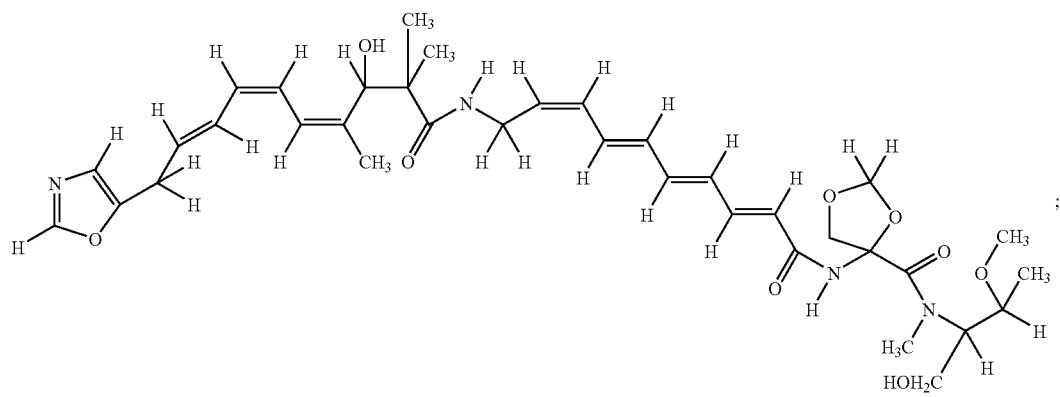
Compound 17
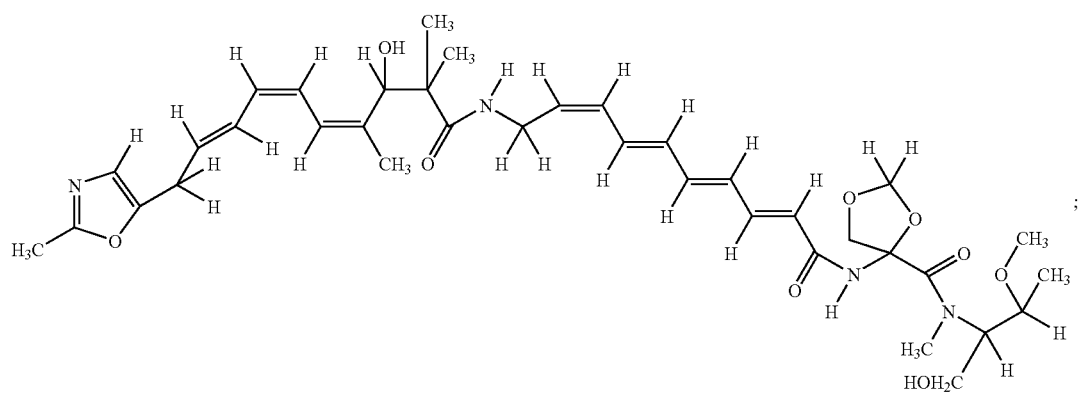
Compound 18
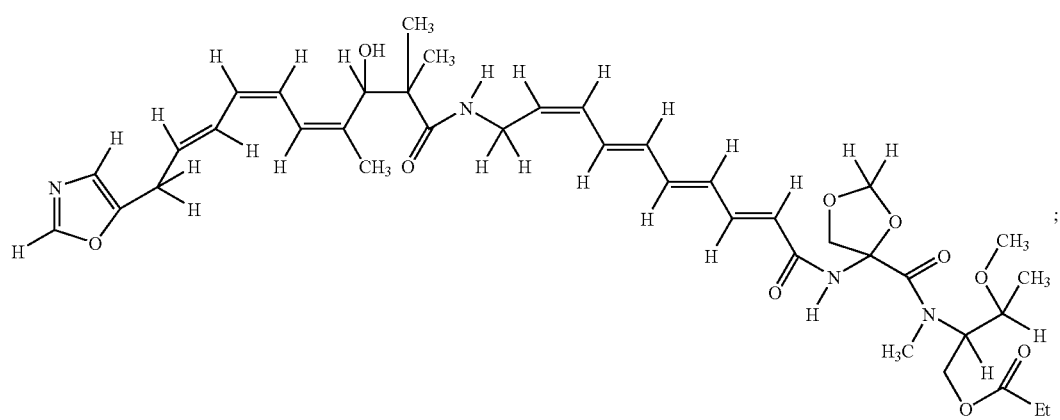
Compound 19
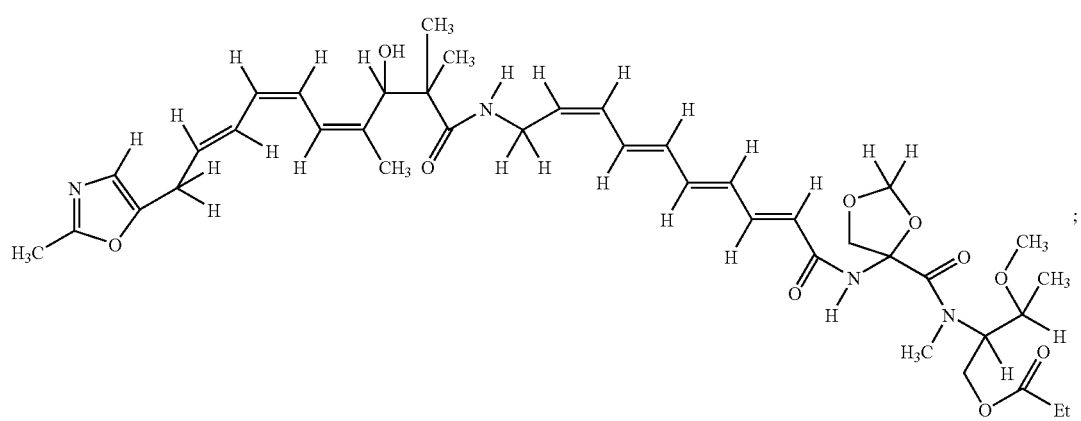
Compound 20

-continued
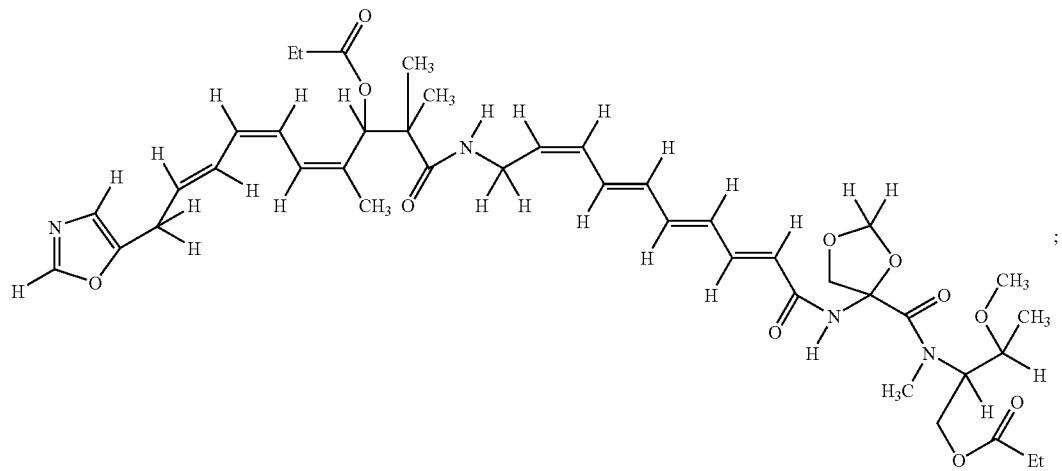
Compound 21
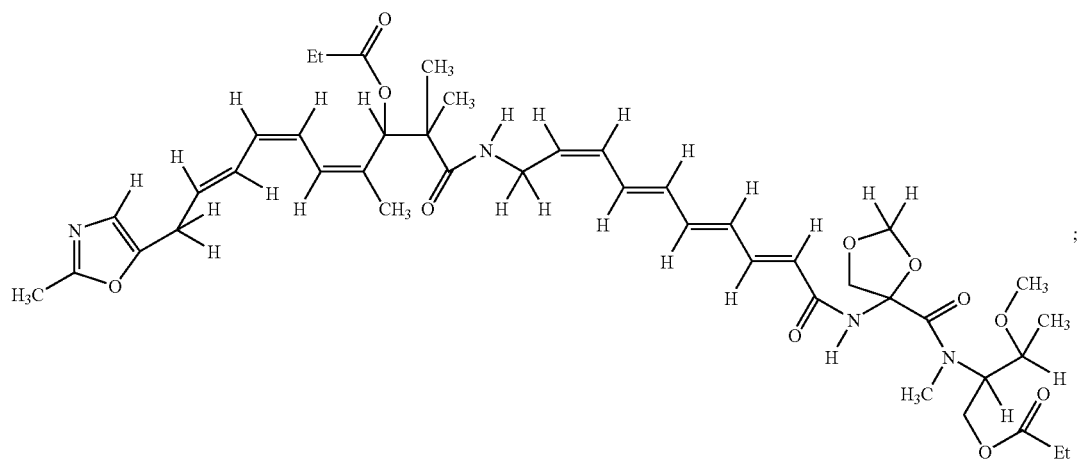
Compound 22
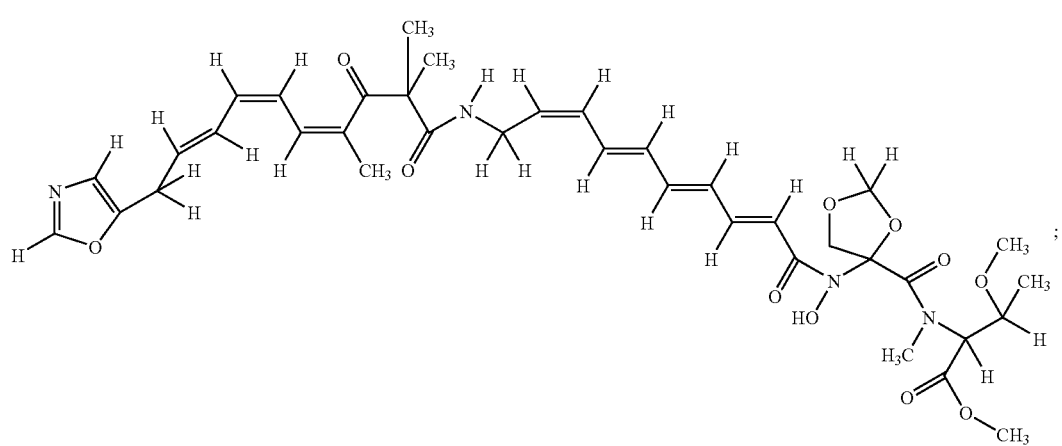
Compound 23

-continued

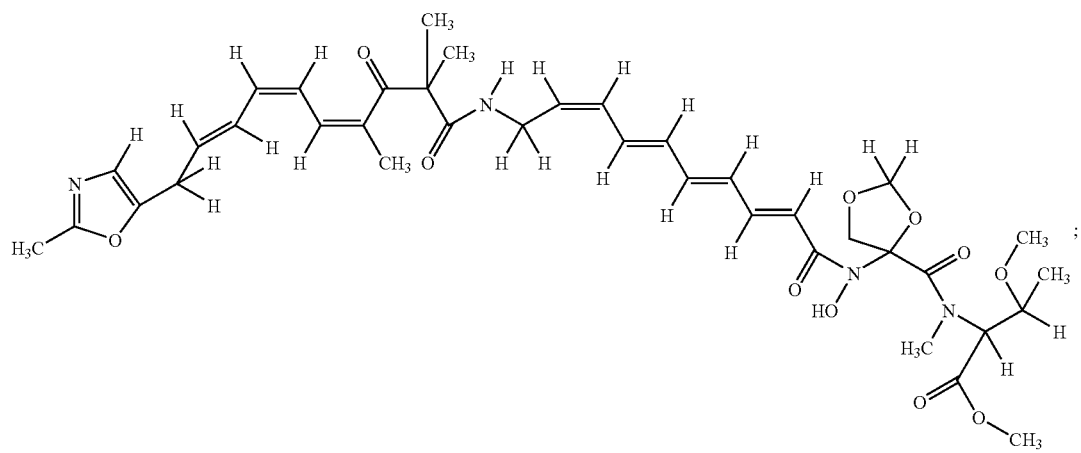

Compound 24

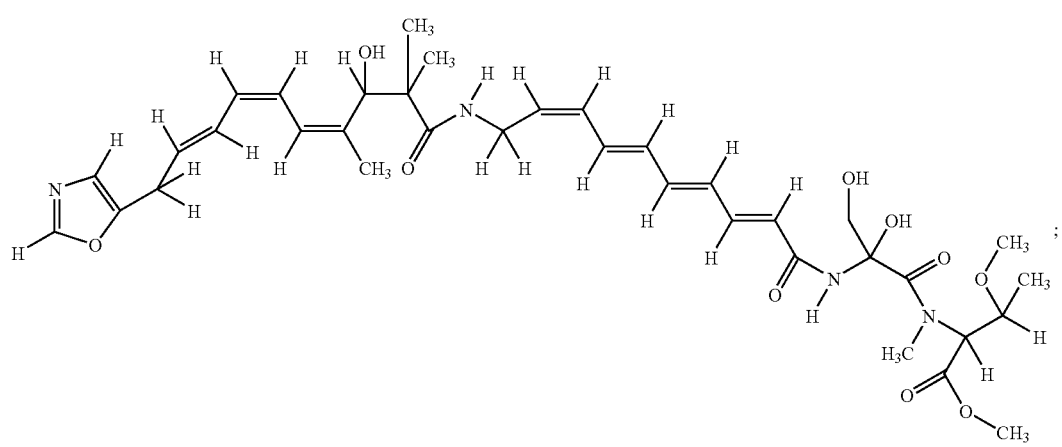

Compound 25

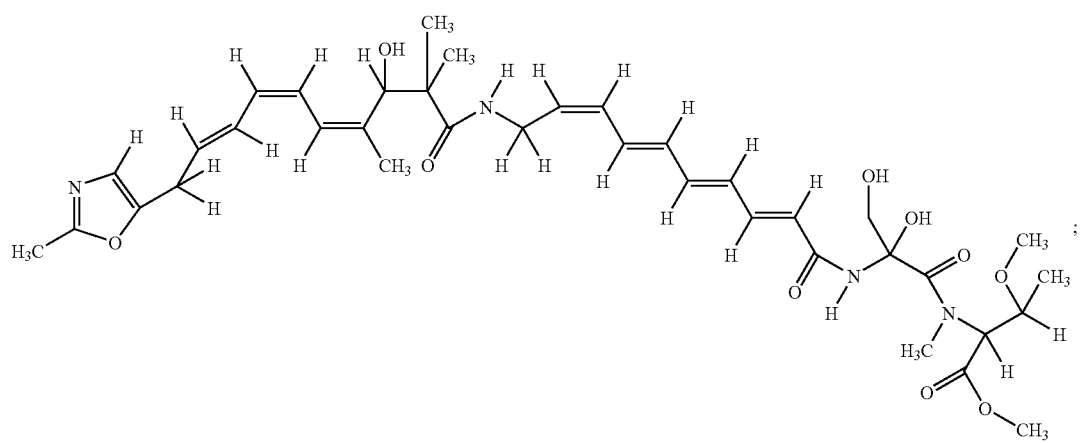

Compound 26 or, a pharmaceutically acceptable salt of any one of Compounds 1-26. Certain embodiments may exclude one or more of the compounds of Formula I.

III. Pharmaceutical Compositions Comprising the Compounds of the Invention

In another embodiment, the invention relates to pharmaceutical compositions comprising a polyene oxazole of the invention, as described in the preceding section, and a pharmaceutically acceptable carrier as described below. The pharmaceutical composition comprising a compound of the invention is useful as a cytotoxic agent and for inhibiting the growth of cancer cells.

As cytotoxic agents, the compounds of the present invention, or pharmaceutically acceptable salts thereof, can be formulated for oral, intravenous, intramuscular, subcutaneous, intraocular, topical or parenteral administration for the therapeutic or prophylactic treatment of diseases, particularly tumor growth. For oral or parenteral administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate tumor growth (See, e.g., Remington's Pharmaceutical Sciences, Mack Publishing Company, Easton, Pa. and Goodman and Gilman's the Pharmaceutical Basis of Therapeutics, Pergamon Press, New York, N.Y., the contents of which are incorporated herein by reference). The compositions of the present invention can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), 5,239,660 (issued to Leonard), 3,854,480 (issued to Zaffaroni).

The pharmaceutically-acceptable compositions of the present invention comprise one or more compounds of the present invention in association with one or more non-toxic, pharmaceutically-acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloical silica.

Flavoring agents such as peppermint, oil of wintergreen, cherry flavoring or the like can also be used. It may also be desirable to add a coloring agent to make the dosage form more aesthetic in appearance or to help identify the product comprising a compound of the present invention.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica or talc: disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, compounds of the present invention can be dissolved or suspended in any of the commonly used intravenous fluids and administered by infusion. Intravenous fluids include, without limitation, physiological saline or Ringer's™ solution.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A recipient subject refers to a plant, a cell culture or an animal such as an ovine or a mammal including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

Likewise, the methods for using the claimed composition for treating cells in culture utilize art-recognized protocols for treating cell cultures with cytotoxic agent(s) with the only substantial procedural modification being the substitution of the compounds of the present invention for the agents used in the art-recognized protocols.

The compounds of the present invention provide a method for treating tumor growth and pre-cancerous or cancerous conditions. As used herein the term unit dosage refers to a quantity of a therapeutically-effective amount of a compound of the present invention that elicits a desired therapeutic response. As used herein the phrase "therapeutically-effective amount" means an amount of a compound of the present invention that prevents the onset, alleviates the symptoms, or stops the progression of a bacterial or fungal infection or pre-cancerous or cancerous condition. The term "treating" is defined as administering, to a subject, a therapeutically-effective amount of at least one compound of the present invention, both to prevent the occurrence of a bacterial or fungal infection or pre-cancer or cancer condition, or to control or eliminate a bacterial or fungal infection or pre-cancer or cancer condition. The term "desired therapeutic response" refers to treating a recipient subject with a compound of the present invention such that a bacterial or fungal infection or pre-cancer or cancer condition is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the infection or disease state, the age and general health of the recipient subject, the tolerance of the recipient subject to the compound and the type of cancer.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved anti-bacterial, anti-fungal or anti-cancer to treat a recipient subject in need of such treatment.

IV. Methods of Producing the Compounds of the Invention

In one embodiment, Compounds 1 and 2 are obtained by cultivating strain of *Streptomyces sparsogenes* NRRL 2940. *Streptomyces sparsogenes* strain NRRL 2940 is available from the Agricultural Research Service Culture Collection, National Center for Agricultural Utilization Research, 1815 N. University Street, Peoria Ill. 61604, USA. However, it is to be understood that the present invention is not limited to use of the particular strain NRRL 2940. Rather, the present invention contemplates the use of other organisms producing Compound 1 or Compound 2.

Mutants or variants of NRRL2940 can be derived from this organism by known means such as X-ray irradiation, ultraviolet irradiation, treatment with a chemical mutagen such as a nitrogen mustard, phage exposure, antibiotic resistance selection and the like. One improved strain created for production of Compound 1 and Compound 2 is *Streptomyces sparsogenes*. [S03]022 which was deposited on May 27, 2004, with the International Depositary Authority of Canada (IDAC), Bureau of Microbiology, Health Canada, 1015 Arlington Street, Winnipeg, Manitoba, Canada R3E 3R2, under Accession No. 270504-04. The deposit of the strain was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112.

Thus, the compounds of the invention may be biosynthesized by various microorganisms, including but not limited to bacteria of the order Actinomycetales, also referred to as actinomycetes. Non-limiting examples of members belonging to the genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of actinomycetes is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the actinomycetes," *Annu. Rev. Microbiol.* (1994) 48:257-289, each is hereby incorporated by reference in its entirety, for genera that may synthesize the compounds of the invention.

An actinomycetes strain is selected and cultivated in culture medium containing known nutritional sources for actinomycetes, such media having assimilable sources of carbon, nitrogen, plus optional inorganic salts and other known growth factors at a pH of about 6 to about 9. Suitable media components include, but are not limited to, glucose, sucrose, mannitol, lactose, cane molasses, soluble starch, corn starch, corn dextrin, potato dextrin, linseed meal, corn steep solids, corn steep liquor, Distiller's Solubles™, dried yeast, yeast extract, malt extract, Pharmamedia™, glycerol, N-Z amine A, soybean powder, soybean flour, soybean meal, beef extract, meat extract, fish meal, Bacto-peptone, Bacto-tryptone, casamino acid, thiamine, L-glutamine, L-arginine, tomato paste, oatmeal, $MgSO_4.7H_2O$, $MgSO_4$, $MgCl_2.6H_2O$, $CaCO_3$, NaCl, Na acetate, $KH_2PO_4$, $K_2HPO_4$, $K_2SO_4$, $Na_2HPO_4$, $FeSO_4.7H_2O$, $FeCl_2.4H_2O$, ferric ammonium citrate, KI, NaI, $(NH_4)_2SO_4$, $NH_4H_2PO_4$, $NH_4NO_3$, $K_2SO_4$, $ZnCl_2$, $ZnSO_4.7H_2O$, $ZnSO_4.5H_2O$, $MnCl_2.4H_2O$, $MnSO_4$, $CuSO_4.5H_2O$, $COCl_2.2H_2O$, phytic acid, casamino acid, proflo oil and morpholinopropanesulfonic acid (MOPS). Non-limiting examples of growth media are provided in Table 1 below.

TABLE 1

Examples of Growth Media for Production of Compound 1 and 2

| Component | DA | DZ | ET | JA | MY | NA | QB | VB |
|---|---|---|---|---|---|---|---|---|
| Glucose | 10 | 5 | | | | | 6 | 10 |
| Sucrose | | | | | | | | 20 |
| Maltose | | | | 4 | | | | |
| Cane molasses | 10 | 10 | 60 | | | 10 | | 20 |
| Soluble starch | 5 | 15 | 20 | | | | 5 | |
| Corn starch | | | | 30 | | | | |
| Potatoe dextrin | 20 | | | | | | | |
| Corn steep solids | 5 | | | | | | 2.5 | |
| Corn steep liquid | | | | 15 | | | | |
| Malt extract | | | | 35 | 10 | | | |
| Yeast extract | | | | | 4 | | | |
| Pharmamedia | | | | 15 | | | 5 | |
| Glycerol | 10 | | | | | 20 | | |
| Soybean flour | 5 | | | | | | | |
| Soytonpeptone | | | | | | | | 5 |
| Fish meal | | 10 | 20 | | | | | |
| Bacto-peptone | | | | | | 1 | | |
| $MgSO_4.7H_2O$ | 0.5 | | | | | | | |
| $CaCO_3$*[1] | 3 | 5 | 2 | 2 | | 4 | | 2.5 |
| $FeCl_2.4H_2O$ | 0.1 | | | | | | | |
| NaI | | | | | 0.5 | | | |
| $ZnCl_2$ | 0.1 | | | | | | | |
| $MnCl_2.4H_2O$ | 0.1 | | | | | | | |
| $CuSO_4.5H_2O$ | | | | | 0.1 | | | |
| Phytic acid | 1 | | | | | | | |

TABLE 1-continued

Examples of Growth Media for Production of Compound 1 and 2

| Component | DA | DZ | ET | JA | MY | NA | QB | VB |
|---|---|---|---|---|---|---|---|---|
| Casamino acid | | | | | | 5 | | |
| Porflo oil | | | | | | | | 2 |

Ingredients are in gm/L. The pH is adjusted to 7 except where indicated.
*[1]pH adjusted to 7.3 prior to the addition of $CaCO_3$.

The culture media inoculated with a microorganism producing the compounds of the invention may be aerated by incubating the inoculated culture media with agitation, for example, shaking on a rotary shaker, or a shaking water bath. Aeration may also be achieved by the injection of air, oxygen or an appropriate gaseous mixture to the inoculated culture media during incubation. Microorganisms are cultivated at incubation temperatures of about 20° C. to about 40° C. for about 3 to about 40 days.

Following cultivation, the compound produced by the microorganism can be extracted and isolated from the cultivated culture media by techniques known to a person skilled in the art and/or disclosed herein, including for example centrifugation, chromatography, adsorption, filtration. For example, the cultivated culture media can be mixed with a suitable organic solvent such as n-butanol, n-butyl acetate or 4-methyl-2-pentanone, the organic layer can be separated for example, by centrifugation followed by the removal of the solvent, by evaporation to dryness or by evaporation to dryness under vacuum. The resulting residue can optionally be reconstituted with for example water, ethanol, ethyl acetate, methanol or a mixture thereof, and re-extracted with a suitable organic solvent such as hexane, carbon tetrachloride, methylene chloride or a mixture thereof. Following removal of the solvent, the compounds may be further purified by the use of standard techniques, such as chromatography.

Polyene oxazoles biosynthesized by a microorganism, such as Compound 1 and Compound 2, may optionally be subjected to random and/or directed chemical modifications to form derivatives or structural analogs of Formula I. The derivatives or structural analogs of Formula I having similar functional activities as Compound 1 or Compound 2 are within the scope of the present invention. Methods known in the art and described herein are used to produce the derivatives or structural analogs of Formula I.

V. Chemical Modification of Compound 1 and Compound 2

Compound 1 or Compound 2 may be modified by standard organic chemistry modification. General principles of organic chemistry required for making and manipulating Compound 1 and Compound 2, including functional moieties, reactivity and common protocols are described, for example, in "Advanced Organic Chemistry", 3$^{rd}$ Edition by Jerry March (1985), which is incorporated herein by reference in its entirety. In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen so that a reaction may be carried out selectively at another reactive site in a polyfunctional compound. General principles for the use of protective groups, their applicability to specific functional groups and their uses are described for example in T. H. Greene and P. G. M. Wuts, Protective Groups in Organic Synthesis, 3$^{rd}$ Edition, John Wiley & Sons, New York (1999).

Those skilled in the art will readily appreciate that many synthetic chemical processes may be used to modify Compound 1 or Compound 2. The following schemes are exemplary of the routine chemical modifications that may be used to produce compounds of Formula I. Any chemical synthetic process known to a person skilled in the art providing the structures described herein may be used and are therefore comprised in the present invention.

Scheme 1: N-Hydroxylamide Reduction

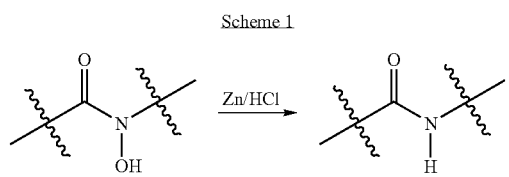

In Scheme 1, an amide is obtained by the reduction of an N-hydroxylamide using a reagent such as Zn in aqueous HCl. Scheme 1 is used to obtain Compound 7 from Compound 1 and Compound 8 from Compound 2.

Scheme 2: Ester Formation, Hydrolysis and Reduction

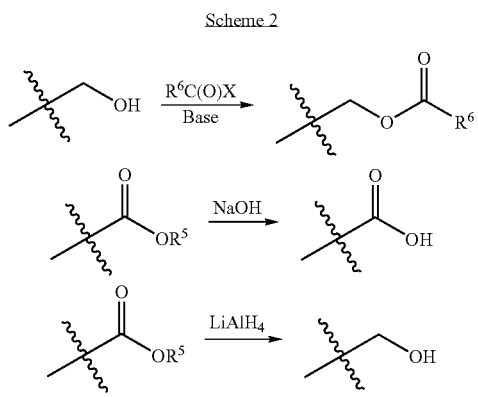

wherein $R^5$ and $R^6$ are as previously described.

In Scheme 2 an alcohol is esterified by standard procedures like addition of RC(O)X (X is a suitable leaving group such as Cl and Br) in the presence of a base such as triethylamine to produce an ester. The ester may be hydrolyzed to a carboxylic acid under suitable conditions such as aqueous sodium hydroxide. The ester may be reduced to a primary alcohol using a reducing agent such as LiAlH$_4$ (lithium aluminum hydride). Scheme 2 is used to obtain Compounds 9, 11, 13 and 15 from Compound 1. Scheme 2 is used to obtain Compounds 10, 12, 14 and 16 from Compound 2. Scheme 2 is used to obtain Compounds 17, 19 and 21 from Compound 7. Scheme 2 is also used to obtain Compounds 18, 20 and 22 from Compound 8.

Scheme 3: Acetal Formation and Hydrolysis

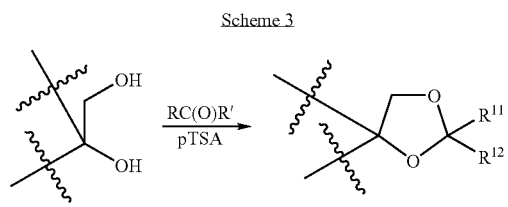

-continued

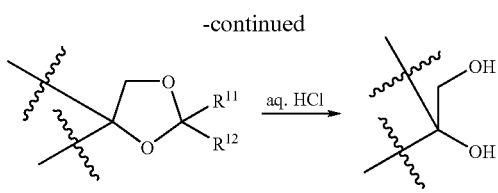

wherein $R^{11}$ and $R^{12}$ are as previously described.

In Scheme 3 an acetal is formed by the reaction of a diol with a ketone or an aldehyde with acid catalysis such as pTSA (p-toluene sulfonic acid) in a dry solvent with removal of the water formed (for example, molecular sieves or Dean Stark apparatus). In Scheme 3 a diol is obtained from the hydrolysis of an acetal in aqueous acidic conditions. Scheme 3 is used to obtain Compounds 3 and 5 from Compound 1. Scheme 3 is used to obtain Compounds 4 and 6 from Compound 2. Scheme 3 is used to obtain Compound 25 from Compound 7. Scheme 3 is also used to obtain Compound 26 from Compound 8.

Scheme 4: Alcohol Oxidation

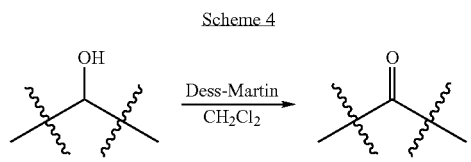

In Scheme 4 a ketone is obtained from the oxidation of a secondary alcohol by an oxidizing agent such as potassium dichromate ($K_2Cr_2O_7$), Dess Martin periodinane (1,1,1-triacetoxy-1,1-dihydro-1,2-benziodoxol-3(1H)one) or Swern oxidation conditions (oxalyl chloride in dimethylsulfoxide). Scheme 4 is used to obtain Compound 23 from Compound 1 and to obtain Compound 24 from Compound 2.

VI. Method of Inhibiting Tumor Growth

In another embodiment, the present invention relates to a method of inhibiting tumor growth. The compound of the invention possess cytotoxic activity. The compounds are effective against mammalian tumor cell lines such as leukemia cell lines, melanoma cell lines, breast carcinoma cell lines, lung carcinoma cell lines, renal carcinoma cell lines, colon carcinoma cell lines, prostate cell lines, bladder cell lines and glioblastoma cell lines. The antitumor method of the invention results in inhibition of tumor cells. The term "inhibition", when used in conjunction with the antitumor method refers to suppression, killing, stasis, or destruction of tumor cells. The antitumor method preferably results in prevention, reduction or elimination of invasive activity and related metastasis of tumor cells. The term "effective amount" when used in conjunction with the antitumor cell method refers to the amount of the compound sufficient to result in the inhibition of mammalian tumor cells.

For the anti-tumor method of the invention, a typical effective dose of the compounds given orally or parenterally would be from about 5 to about 100 mg/kg of body weight of the subject with a daily dose ranging from about 15 to about 300 mg/kg of body weight of the subject.

The following examples illustrate the invention but are not to be construed as limiting. Unless otherwise noted, all reagents were purchased from Sigma Chemical Co. (St. Louis, Mo.), (Aldrich).

EXAMPLE 1

Production of Compound 1 and Compound 2

[S03]022 is a natural mutant of *Streptomyces sparsogenes* NRRL 2940 which was obtained by selection on Tomato paste oatmeal agar containing 25 µg/ml of streptomycin. [S03]022 was used for production of Compounds 1 and 2. Strain [S03]022 grows on agar medium GYM (Glucose 4 g; Yeast extract 4 g; Malt extract 10 g; N-Z Amine A 1 g; NaCl 2 g; Agar 20 g; made up to 1 liter with distilled water adjusting the pH to 7.2 before sterilization) or Tomato paste oatmeal agar (ATCC medium 1360) within 7-10 days appearing as beige-colored vegetative mycelium which after about 3 weeks produces spores with dark gray color.

Strain [$SO_3$]022 was grown for about 3 weeks at 28° C. on several Tomato paste oatmeal agar plates. Spores were collected from each plate into 5 ml sterile distilled water, spun down by centrifugation at 5000 rpm (10 min), the supernatant was decanted and the spores dispersed in 10 ml sterile water and re-centrifuged under the same conditions. Spores were resuspended in 2 ml sterile 25% glycerol and stored at −80° C. In addition to the glycerol stock, spores were resuspended in 15% sterile skim milk and dispensed as 0.5-ml aliquots into glass ampoules and were lyophilized following standard procedures, and sealed under vacuum.

Strain [$SO_3$]022 was maintained and transferred on Tomato paste oat meal agar. A vial containing frozen mycelium or spores was taken out of freezer and kept on dry ice. Under aseptic conditions, a loopful of the frozen stock was taken and streaked on the surface of Tomato paste oatmeal agar plate and incubated at 28° C. for a minimum of 7-10 days until vegetative mycelium appeared. Longer incubation is required for sporulation.

Spores obtained from the strain [S03]022, *Streptomyces sparsogenes* NRRL 2940 were maintained in individual aliquots at −80° C. Under sterile conditions, a loopfull of the frozen culture was taken and streaked on a Tomato paste-oatmeal agar plate (ATCC medium 1360) and incubated at 280 C until a vegetative mycelium appeared (about 15 to about 20 days). Two to three loopfulls of the surface growth on the Tomato paste-oatmeal agar plate were transferred to a 125 ml flask containing 25 ml of sterile medium comprised of 24 g potato dextrin, 3 g beef extract, 5 g Bacto-casitone, 5 g glucose, 5 g yeast extract, and 4 g $CaCO_3$ made up to one liter with distilled water with the pH adjusted to about 7.0. This was incubated at about 28° C. for about 60 hours on a rotary shaker set at about 250 rpm. After the incubation period, an aliquot of about 10 ml was transferred to a 2-L baffled flask containing 500 mL of sterile medium VB of Table 1, adjusted to a pH of about 7.0. This was incubated at about 28° C. in a rotary shaker set at about 250 rpm for about 7 days providing the fermentation broth.

Compound 1 and Compound 2 were also produced under growth media DA, DZ, ET, JA, MY, NA. and QB of Table 1. Compound 1 and Compound 2 were further produced using spores obtained from *Streptomyces sparsogenes* NRRL 2940.

EXAMPLE 2

Isolation

At harvest, the fermentation broth of Example 1 was centrifuged for 10 min and the solid (mycelia) and liquid (supernatant) components were separated by decantation. To the supernatant liquid 60 mL of HP-20 resin was added and stirred for 20 minutes. The slurry was filtered on a bed of fresh resin (60 ml) sitting on a Buchner funnel. This was washed with 100 mL of water and the eluate saved and labeled extract 5. The column was then washed with 100 mL of a mixture of methanol, water (3:2, v/v), the eluate was saved and labeled extract 3. This was followed with a wash with 100 mL of 100% methanol and a subsequent wash of 100 mL acetonitrile, the combined eluates were saved and labeled extract 4.

To the mycelia approximately 100 mL of 100% methanol was added. The mixture was stirred for about 15 min and centrifuged for approximately 10 min. The methanol supernatant was removed and saved. To the pellet approximately 100 mL of acetone was added, stirred for about 15 min and centrifuged for 10 min, the supernatant was added to the methanol supernatant and labeled extract 1. To the pellet, approximately 100 mL of methanol, water (1:4, v/v) was added, stirred for about 15 min and centrifuged for about 10 min. The supernatant was decanted and labeled extract 2 and the remaining pellet was discarded.

EXAMPLE 3

Purification

Figure 1B:
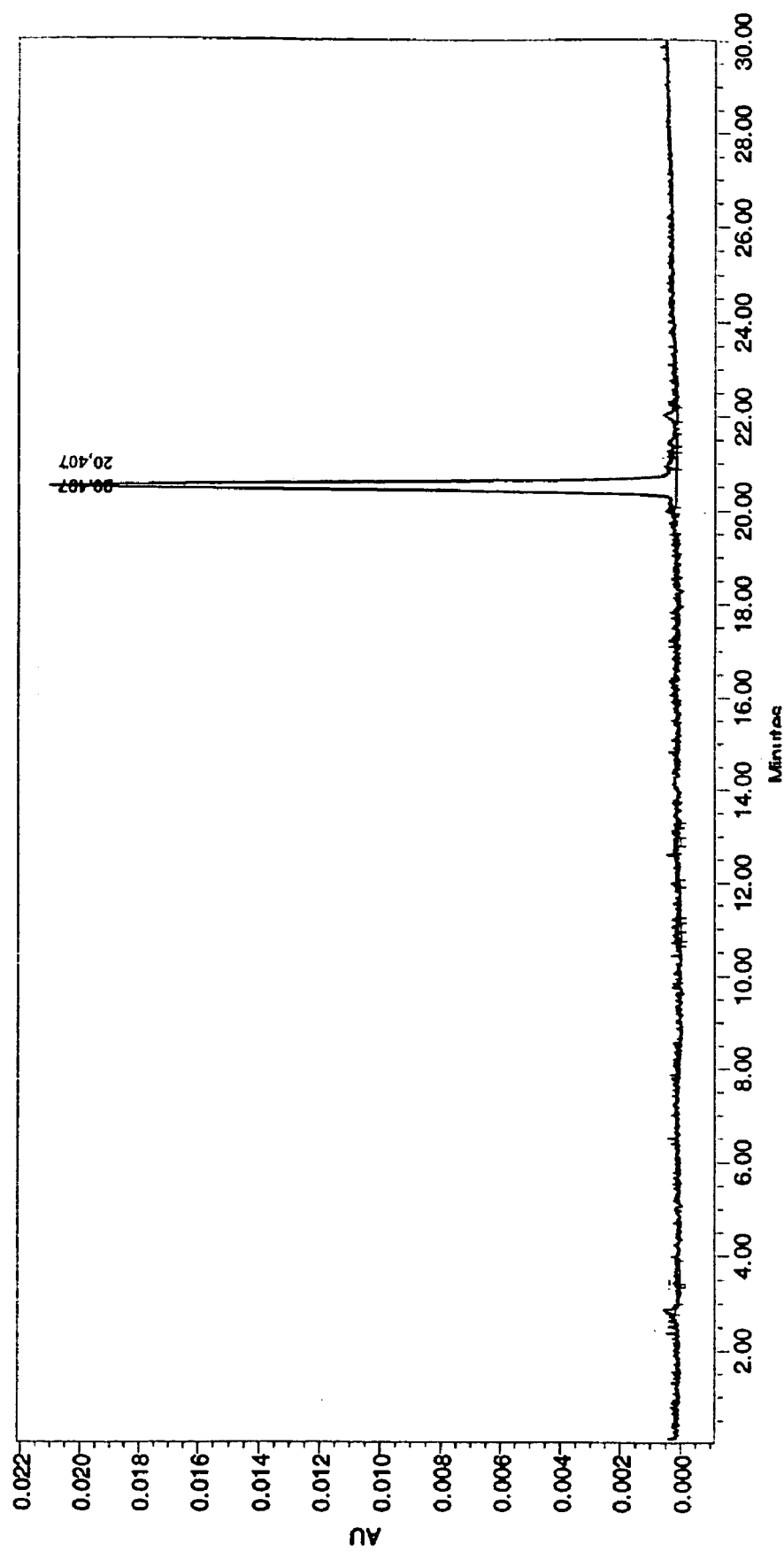
Figure 1C:
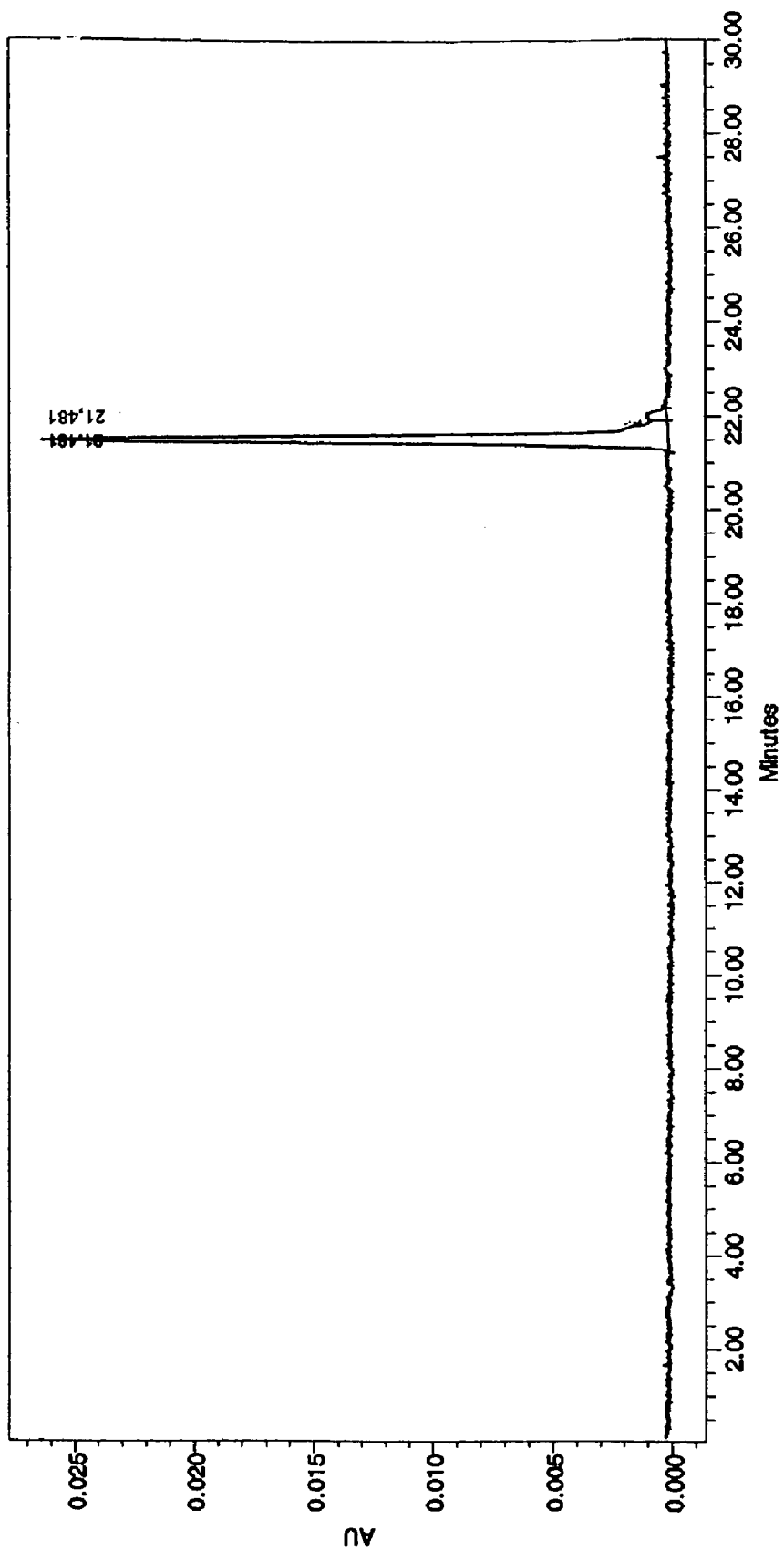

A sample of each extract was transferred to well plates. For extracts 1, 2, 3, and 4 aliquots of 20 µl, 10 µl, 5 µl and 2 µl, and for extract 5 120 µl, 60 µl, 30 µl and 15 µl aliquots were transferred to well plates. The amounts in the well plates were evaporated and or stored at −80° C. Extract 1 from Example 2 was filtered and concentrated on a rotary evaporator and freeze-dried for further fractionation. Initial fractionation was carried out by reversed-phase silica gel chromatography utilizing a STRATA C18-E (50 µm, 70 Å), 10 g, 60 ml tube using a 5-step gradient elution from water-methanol (80:20) to methanol (100%) (200 mL each step). Five fractions were collected, concentrated to dryness under vacuum, and analyzed by HPLC. The HPLC analysis of an active fraction (water-methanol, 20:80) showed two major peaks, with retention times of 20.4 min and 21.4 min, along with some minor peaks. This fraction (dissolved in water-acetonitrile, 10:90) was further purified by reversed-phase semi-preparative HPLC using a mobile phase of water-acetonitrile, (60:40) to (0:100) gradient elution, a flow rate=5.0 mL/min for 35 min to yield Compound 1 (6 mg/L fermentation beer), with a retention time 20.4 min and Compound 2 (8 mg/L fermentation beer) with a retention time of 21.4 min. as shown in FIG. 1. Both compounds were obtained as cream colored amorphous powders. The purity of the Compounds 1 and 2 was established by HPLC (water-acetonitrile, 40:60, using a 30 min. linear gradient, and a flow rate=1.0 ml/min).

EXAMPLE 4

Structure Data

Figure 3:
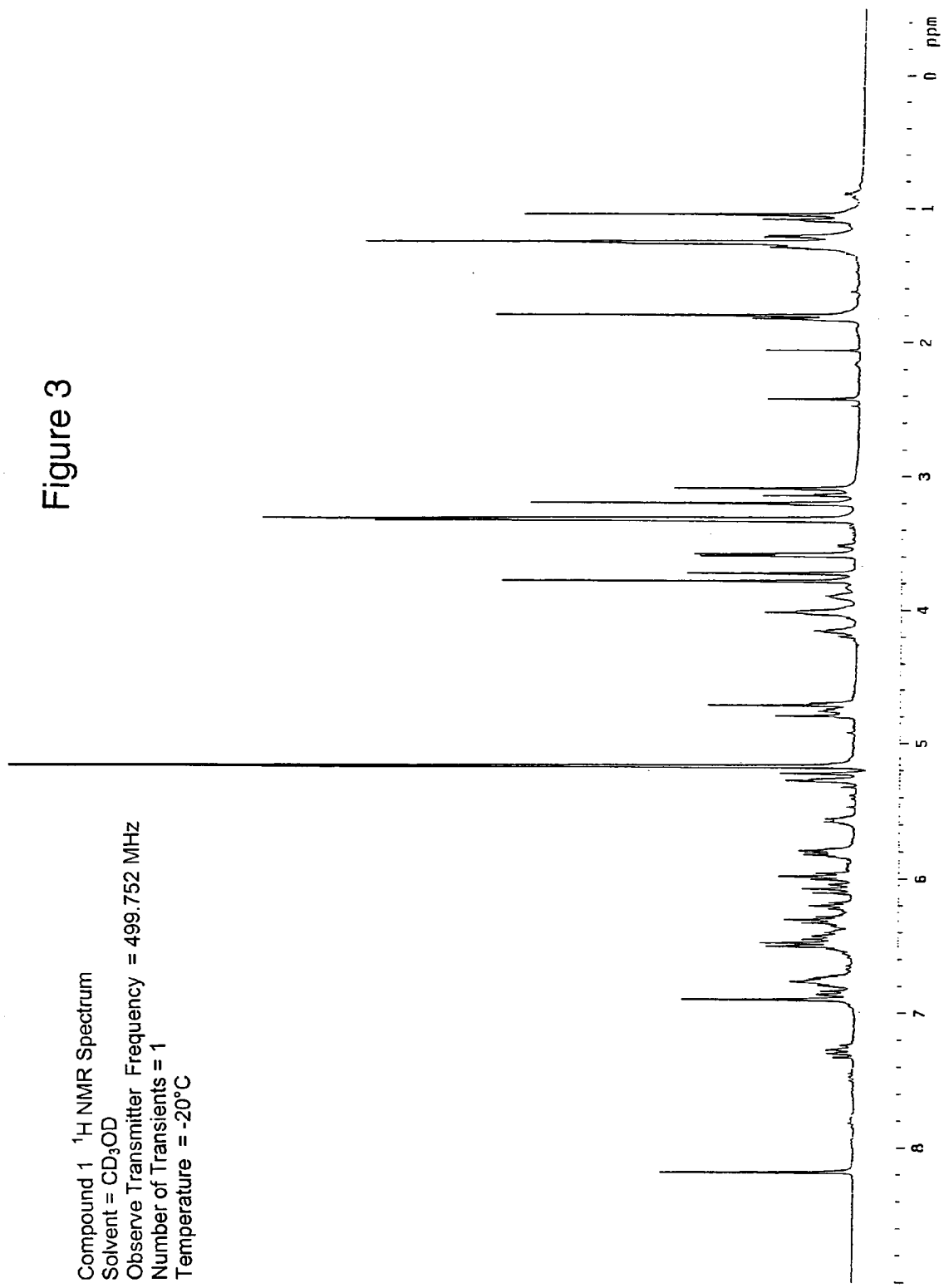
FIG. 3 is a $^1$H NMR spectrum in $CD_3OD$ solvent for Compound 1.
Figure 4:
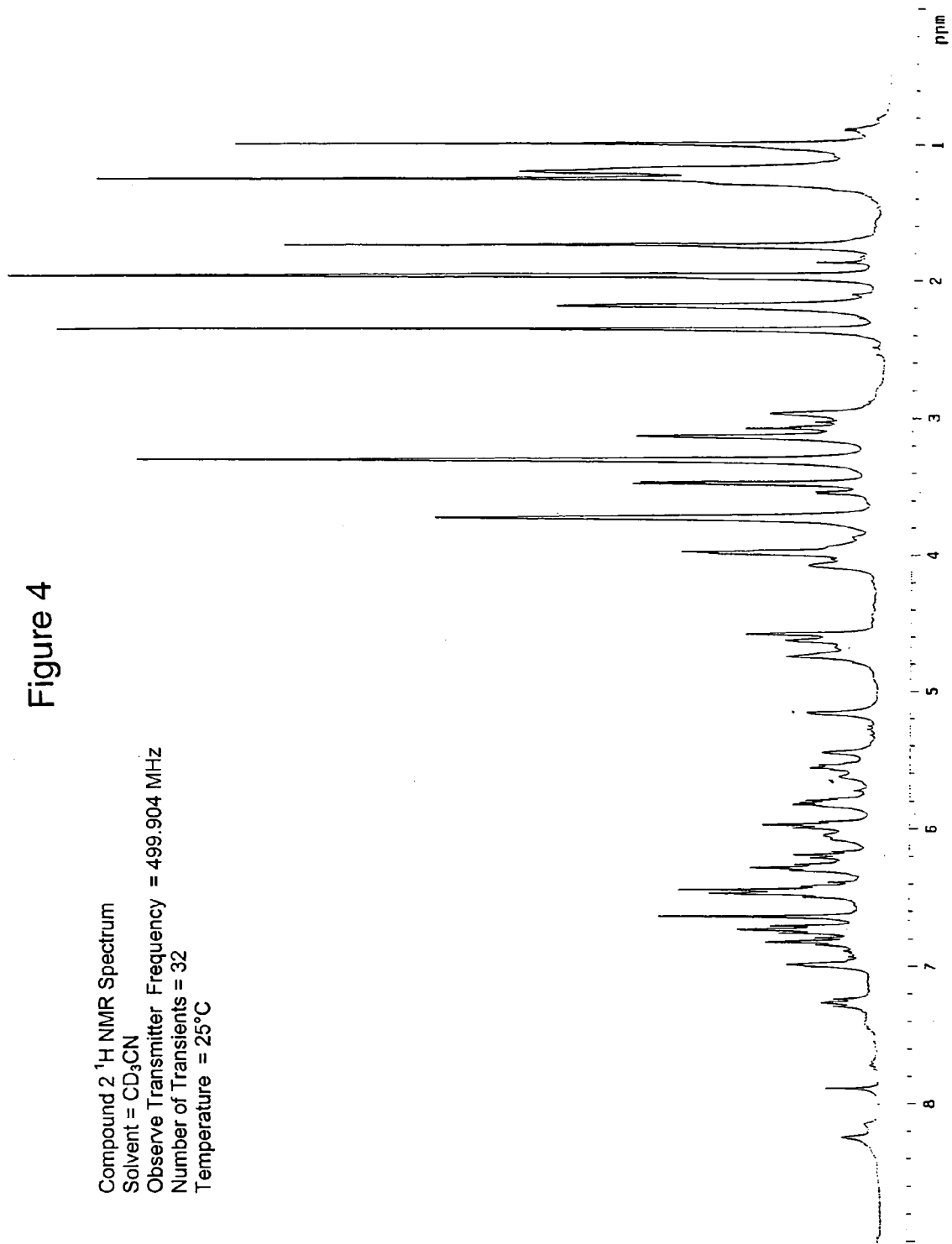
FIG. 4 is a $^1$H NMR spectrum in $CD_3CN$ solvent for Compound 2.
Figure 5:
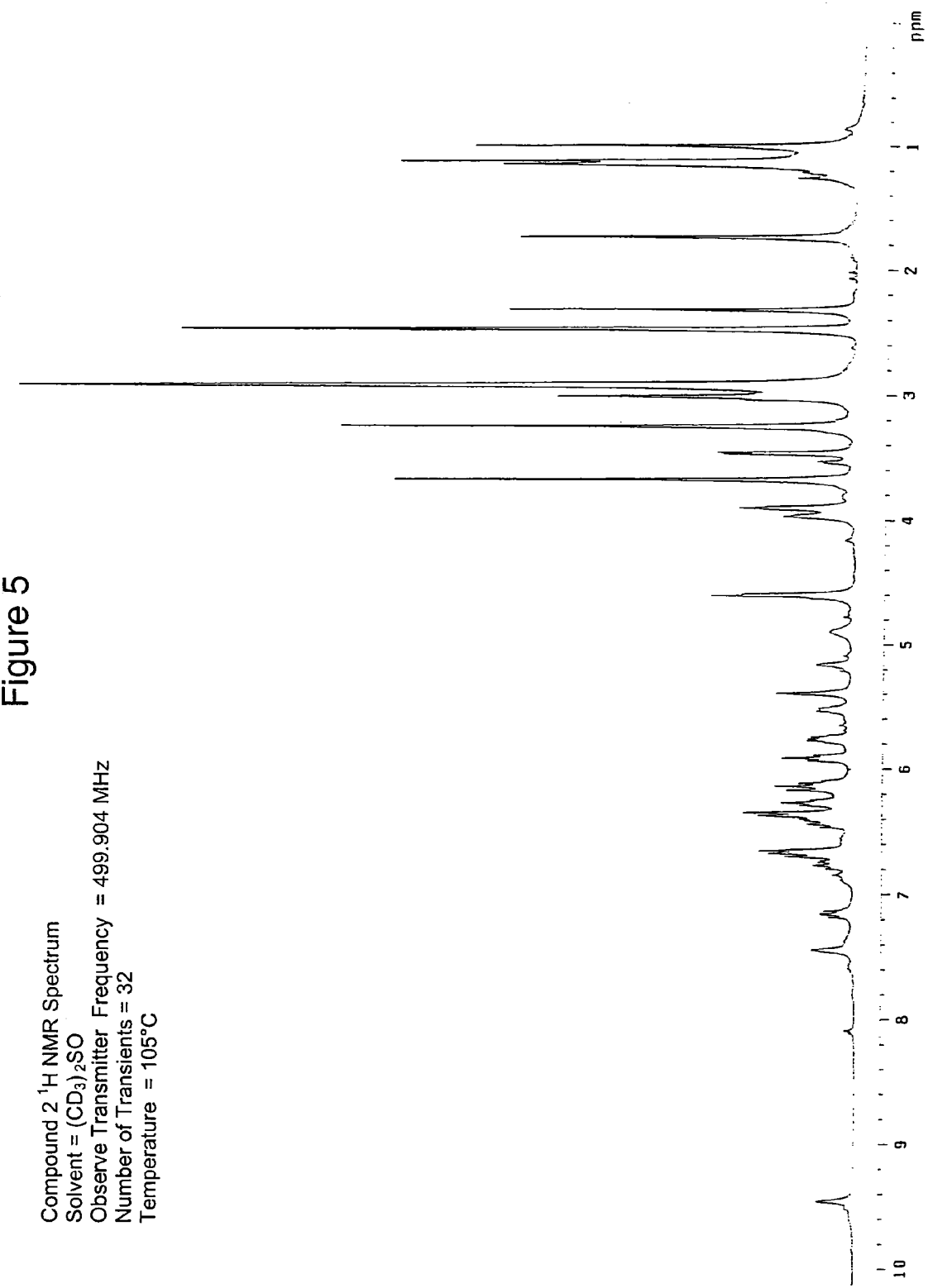
FIG. 5 is a $^1$H NMR spectrum in $(CD_3)_2$ SO solvent for Compound 2.
Figure 6:
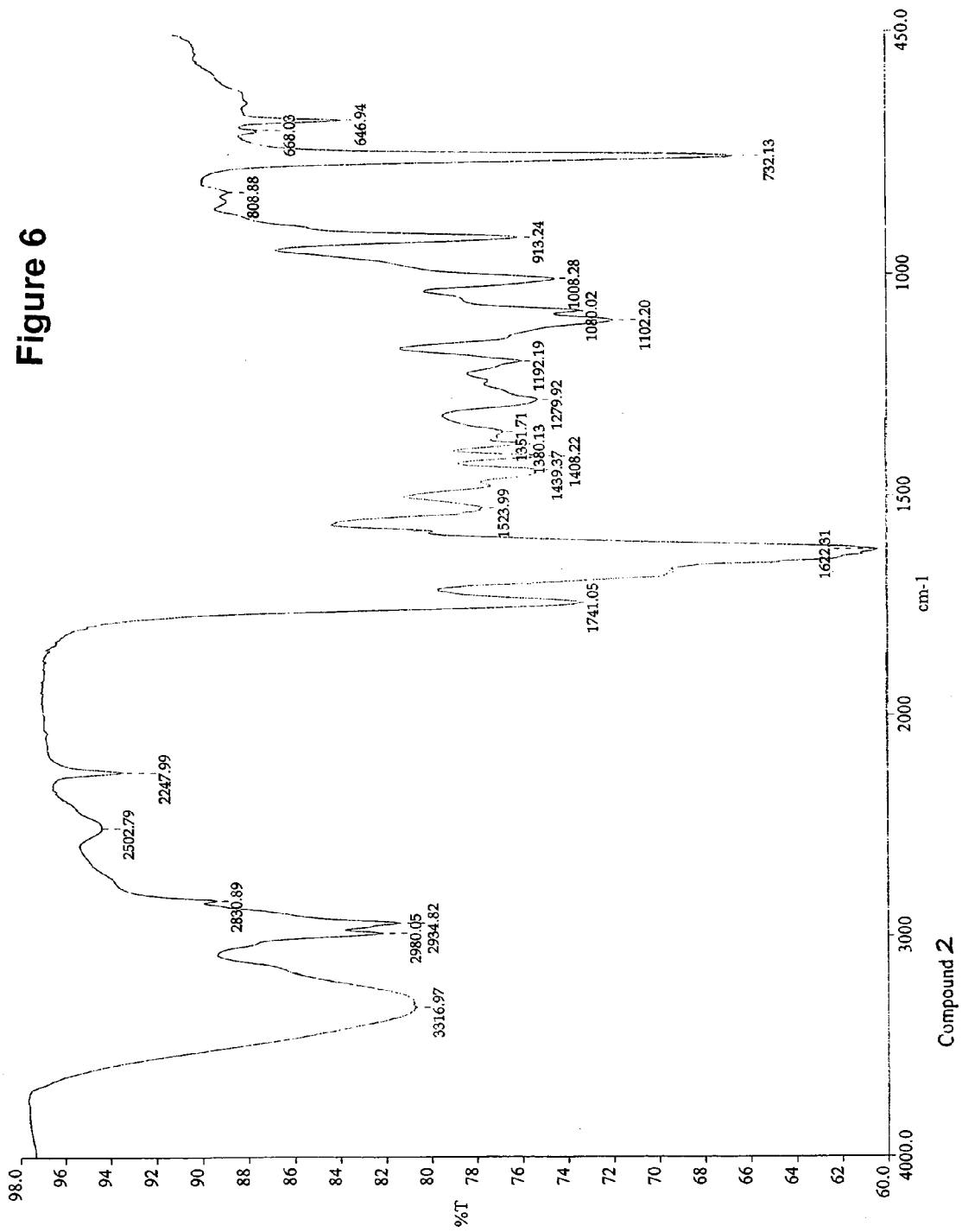
FIG. 6 is an infrared spectrum for Compound 2.

The structure of the Compounds 1 and 2 was derived from analysis of spectroscopic data including Mass, UV, IR, and NMR spectroscopy. Mass was determined by electrospray mass spectrometry; Ultravioletspectra displayed UV $\lambda_{max}$ 276, 340 nm (FIG. 2). NMR data, collected in acetonitrile-$d_3$, methanol-d4 or DMSO-d6 including proton (FIGS. 3, 4 & 5), carbon-13 and multidimensional pulse sequences gDQCOSY, gHSQC, gHMBC, and TOCSY were measured at 500 MHz. The IR spectrum of Compound 1 was measured as CHCl$_3$ smear on NaCl plate (FIG. 6).

TABLE 2

$^1$H and $^{13}$C NMR data of Compound 1 in CD$_3$OD and of Compound 2 in CD$_3$CN

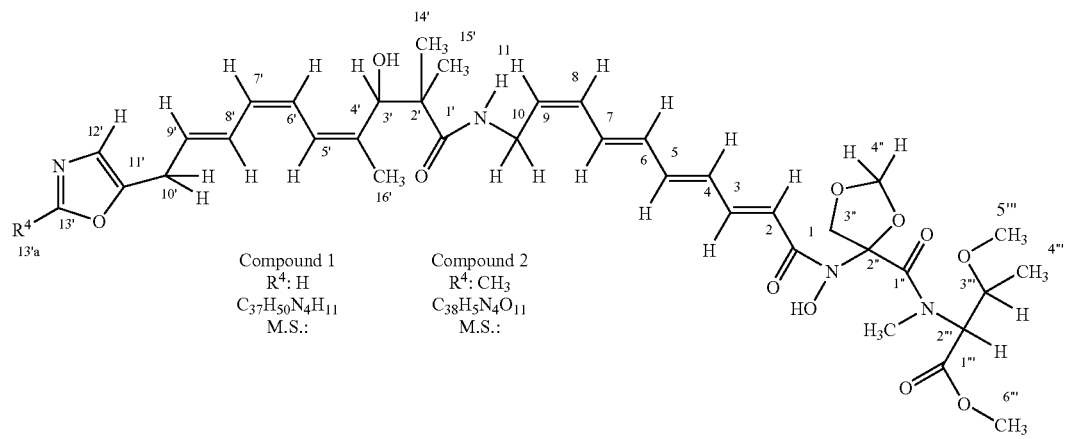

Compound 1
R$^4$: H
C$_{37}$H$_{50}$N$_4$H$_{11}$
M.S.:

Compound 2
R$^4$: CH$_3$
C$_{38}$H$_5$N$_4$O$_{11}$
M.S.:

| | δ$_H$ (ppm) of 1 and 2 | | δ$_C$ (ppm) of 1 and 2 | | |
|---|---|---|---|---|---|
| Position | 1 | 2 | 1 | 2 | Group |
| 1 | — | — | 165.1 | 164.0 | C |
| 2 | 6.08 | 6.01 | 122.4 | 124.1 | CH |
| 3 | 7.29 | 7.20 | 143.3 | 142.3 | CH |
| 4 | 6.47 | 6.45 | 130.4 | 131.1 | CH |
| 5 | 6.78 | 6.70 | 141.3 | 140.8 | CH |
| 6 | 6.43 | 6.40 | 133.9 | 133.5 | CH |
| 7 | 6.87 | 6.82 | 128.7 | 131.7 | CH |
| 8 | 6.20 | 6.20 | 130.7 | 130.5 | CH |
| 9 | 5.58 | 5.52 | 130.1 | 130.5 | CH |
| 10 | 3.9–4.01 | 3.95 | 36.9 | 37.4 | CH$_2$ |

TABLE 2-continued $^1$H and $^{13}$C NMR data of Compound 1 in CD$_3$OD and of Compound 2 in CD$_3$CN

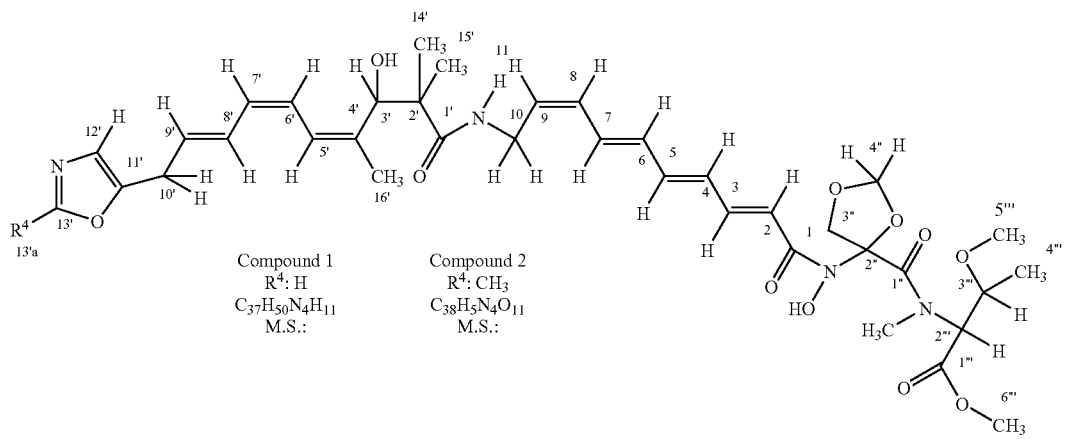

Compound 1
R$^4$: H
C$_{37}$H$_{50}$N$_4$H$_{11}$
M.S.:

Compound 2
R$^4$: CH$_3$
C$_{38}$H$_5$N$_4$O$_{11}$
M.S.:

| | δ$_H$ (ppm) of 1 and 2 | | δ$_C$ (ppm) of 1 and 2 | | |
|---|---|---|---|---|---|
| Position | 1 | 2 | 1 | 2 | Group |
| 11 | NA[a] | 6.95 | — | — | NH |
| 1' | — | — | 178.7 | 178.5 | C |
| 2' | — | — | 46.1 | 45.3 | C |
| 3' | 4.72 | 4.55 | 74.4 | 75.5 | CH |
| 4' | — | — | 139.5 | 140.3 | C |
| 5' | 6.49 | 6.45 | 124.3 | 124.9 | CH |
| 6' | 6.30 | 6.27 | 124.8 | 124.9 | CH |
| 7' | 5.98 | 5.97 | 129.0 | 128.9 | CH |
| 8' | 6.77 | 6.72 | 128.7 | 128.7 | CH |
| 9' | 5.82 | 5.79 | 129.0 | 130.0 | CH |
| 10' | 3.58 | 3.45 | 28.8 | 29.5 | CH$_2$ |
| 11' | — | — | 152.3 | 151.1 | C |
| 12' | 6.91 | 6.91 | 121.8 | 123.4 | CH |
| 13' | 8.22 | — | 151.7 | 160.3 | C(H)[b] |
| 13'a | — | 2.33 | — | 13.9 | CH$_3$ |
| 14' | 1.06 | 0.97 | 20.9 | 21.9 | CH$_3$ |
| 15' | 1.27 | 1.24 | 25.0 | 26.1 | CH$_3$ |
| 16' | 1.82 | 1.72 | 19.2 | 19.7 | CH$_3$ |
| 1" | — | — | 170.3 | 168.7 | C |
| 2" | — | — | NA | NA | C |
| 3" | NA | NA | NA | NA | CH$_2$ |
| 4" | 4.79, 5.24 | 4.72, 5.44 | 102.1 | 102.2 | CH$_2$ |
| 1''' | — | — | 170.0 | 170.3 | C |
| 2''' | 5.3 | 5.14 | 60.8 | 61.2 | CH |
| 3''' | 4.17 | 4.08 | 76.7 | 78.0 | CH |
| 4''' | 1.27 | 1.12 | 15.8 | 15.0 | CH$_3$ |
| 5''' | 3.30 | 3.29 | 56.5 | 56.8 | CH$_3$ |
| 6''' | 3.72–3.78 | 3.71 | 52.0 | 52.5 | CH$_3$ |
| 7''' | 3.20–3.30 | 3.12 | 35.9 | 35.1 | CH$_3$ |

[a] NA: not assigned
[b] CH in Compound 1, quaternary carbon C in Compound 2

Assignment of the linear polyene portion ($C_{1-10}$ and $C_{1'-16'}$) was easily accomplished by routine NMR analysis. The modified serine-threonine structure assignment was supported by gHMBC NMR proton—carbon long range correlation data as follow:

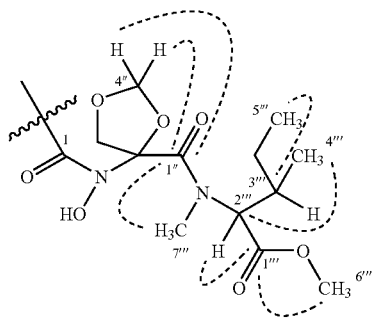

For a purpose of clarity, the NMR data of only one rotamer were included in the table.

EXAMPLE 5

In Vitro Cytotoxicity Efficacy on Cancer Cell Lines

The cell lines listed below have been used to characterize the cytotoxicity of representative compounds of Formula I. The cell lines were shown to be free of mycoplasma infection and were maintained on the appropriate media and supplemented with 10% heat-inactivated fetal bovine serum and 1% penicillin-streptomycin, under 5% $CO_2$ at 37° C. Cells were passaged two to three times per week. Cellular viability was examined by staining with trypan blue and only flasks where cell viability was >95% were used to determine cytotxicity.

Exponentially growing cells ($1-3\times10^3$ cells per 100 µl) were seeded in 96-well plates and incubated for 16 h. Cells were then exposed continuously to various concentrations of compounds of Formula I in serum-supplemented medium. Cell survival was evaluated 96 h later by replacing the culture media with 150 µl fresh medium containing 10 mM 4-(2-hydroxyethyl)-1-piperazineethanesulfonic acid buffer, pH 7.4. Next, 50 µl of 2.5 mg/ml of 3-(4,5-dimethylthiazo-2-yl)-2,5-diphenyltetrazolium bromide (MTT; Sigma, St. Louis, Mo.) in phosphate buffer solution, pH 7.4, was added. After 3-4 h of incubation at 37° C., the medium and MTT was removed, and 200 µl of dimethylsulfoxide was added to dissolve the precipitate of reduced MTT followed by addition of 25 µl glycine buffer (0.1 M glycine plus 0.1 M NaCl, pH 10.5). The absorbance was determined at 570 nm with a microplate reader (BIORAD). Cell survival was estimated as % of cells treated with the vehicle alone. Cytotoxicity results of Compound 1 and Compound 2 are shown in Table 3.

TABLE 3

|  | In Vitro Cytotoxicity Data | | | |
|---|---|---|---|---|
|  | CDDP | Compound 1 | Compound 2 | Curromycin (NCI data log $GI_{50}$) |
| MDA-MD-231 (breast/human) | 0.8* (Log −6.10 M) | 12.9* (Log −4.88 M) | 13.2* (Log −4.88 M) | Log −4.6 M |
| HCT116 (colon/human) | 2.3* (Log −5.6 M) | 24.8* (Log −4.60 M) | 27.5* (Log −4.56 M) | Log −4.8 M |
| PC3 (prostate/human) | 0.6* (Log −6.15 M) | 20.7* (Log −4.69 M) | 20.7* (Log −4.67 M) | Log −6.6 M |
| A498 (renal/human) | 2.4* (Log −5.62 M) | 15.6* (Log −4.78 M) | 13.1* (Log −4.88 M) | Log −4.5 M |
| P388 (leukemia/mouse) | 0.3 (Log −6.63 M) | 6.3 (Log −5.19 M) | 8.1 (Log −5.05 M) | ~0.2 Log −6.7 M |
| EKVX (lung/human) | 1.5 (Log −5.80 M) | 37.4 (Log −4.42 M) | 23.9 (Log −4.62 M) | Log −6.5 M |
| B16 (melanoma/mouse) | 25.9 (Log −4.58 M) | 44.8 (Log −4.34 M) | 45.5 (Log −4.34 M) | ~3.5 Log −5.45 M |
| T24 (bladder/human) | 1.1 (Log −5.96 M) | 30.5 (Log −4.51 M) | 18.9 (Log −4.72 M) | ND |
| SF-295 (glioblastoma/human) | 1.3 (Log −5.90 M) | 27.1 (Log −4.56 M) | 17.5 (Log −4.75 M) | Log −6.3 M |
| HRE (renal/normal, human) | 0.6 (Log −6.20 M) | 8.8 (Log −5.05 M) | 20.2 (Log −4.69 M) |  |

*Mean from 3 independent experiments

EXAMPLE 6

Synthesis of Compound 5 by Hydrolysis of Compound 1

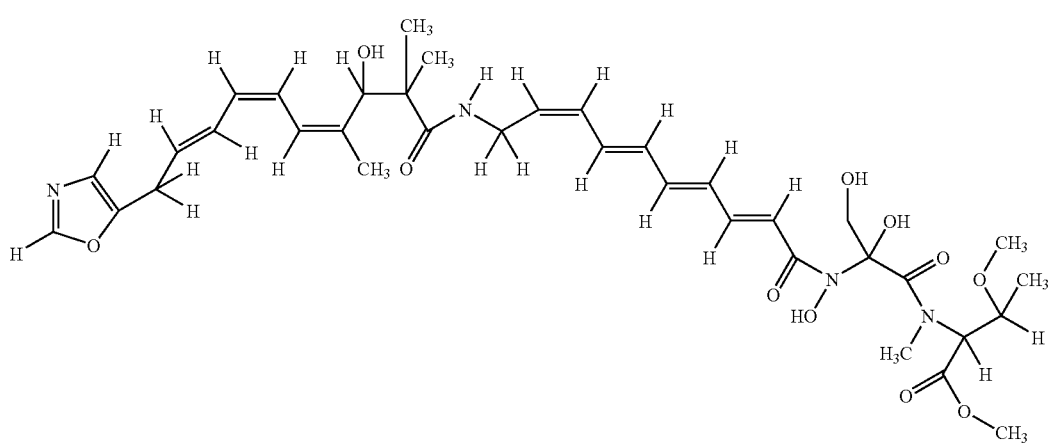

Compound 5

A solution of Compound 1 in a 1:1 mixture of THF and 1 M HCl is heated under reflux overnight. The resulting mixture is extracted with ethyl acetate. Organic layer is washed with brine, dried over magnesium sulfate, filtered and concentrated in vacuo to give Compound 1 after silica-gel column chromatography using a mixture of methanol and methylene chloride as eluent.

EXAMPLE 7

Synthesis of Compound 3 by Acetalisation of Compound 5

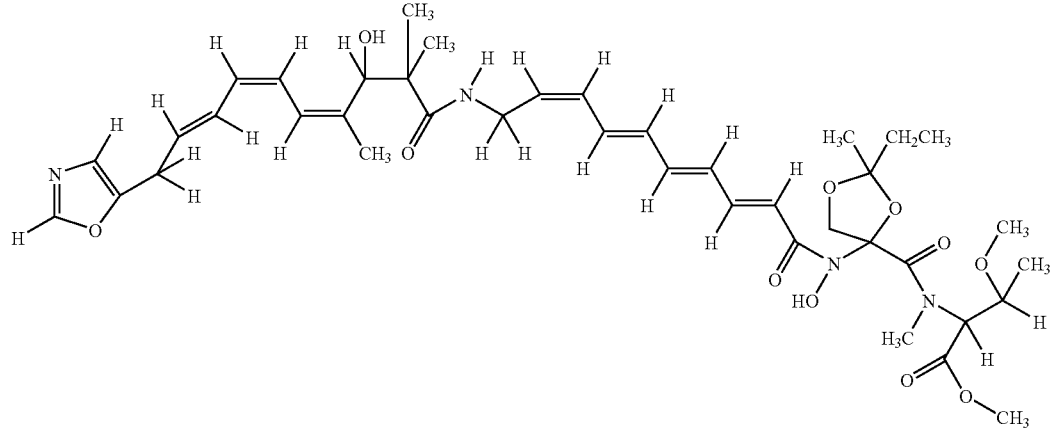

Compound 3

To a solution of Compound 5 and 2-butanone in benzene, is added 0.1 equivalent of p-tolunesulfonic acid. The reaction mixture is heated overnight under reflux using a Dean Stark apparatus to eliminate water. Solvent is removed in vacuo and the residue is purified by silica gel column chromatography using a mixture of methanol and methylene chloride as eluent to give Compound 3.

EXAMPLE 8

Synthesis of Compound 9 from Esterification of Compound 1

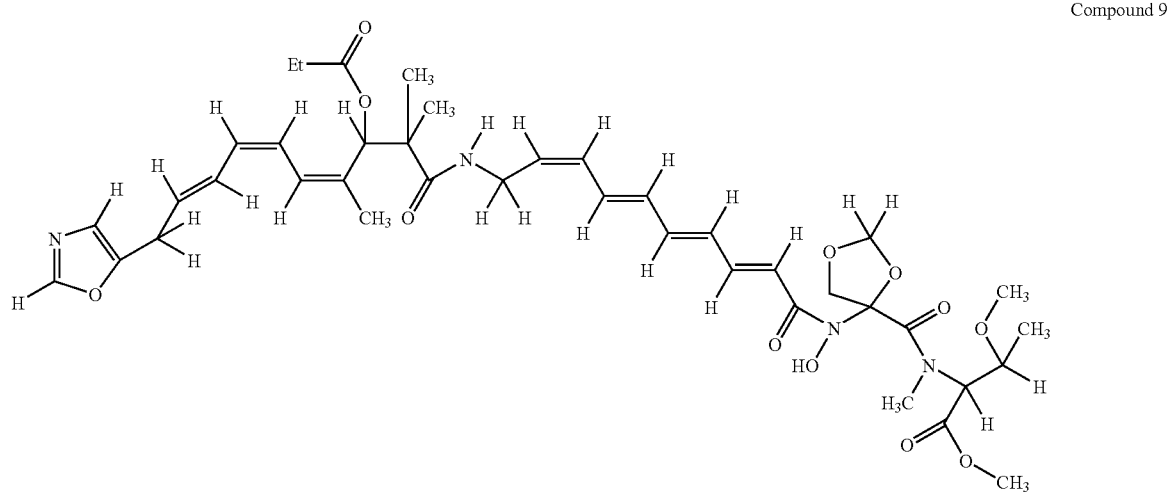

Compound 9

To a solution of Compound 1 and triethylamine in tetrahydrofurane (THF) is added propionyl chloride and the reaction stirred overnight. Triethylamine hydrochloride salt is filtered through a Celite® 545 pad. The filtrate is diluted in ether and washed with water and brine, dried over magnesium sulfate, filtered and concentrated in vacuo. The residue is purified by silica gel column chromatography using a mixture of methanol and methylene chloride as eluent to give Compound 9.

EXAMPLE 9

Synthesis of Compound 13 from Hydrolysis of Compound 1

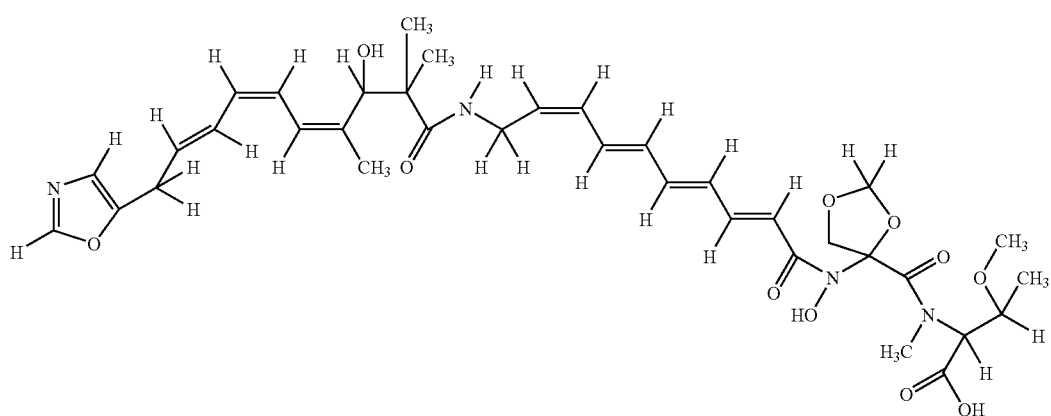

Compound 13

Compound 1 is dissolved in 2M sodium hydroxide aqueous solution using a minimum amount of methanol and stirred overnight. The reaction mixture is acidified using 1 M hydrochloric acid and extracted with ethyl acetate. Organic layer is separated, washed with brine, dried over magnesium sulfate, filtered and concentrated in vacuo. The residue is purified by silica gel column chromatography using a mixture of methanol and methylene chloride as eluent to give Compound 13.

EXAMPLE 10

Synthesis of Compound 17 from the Reduction of Compound 7

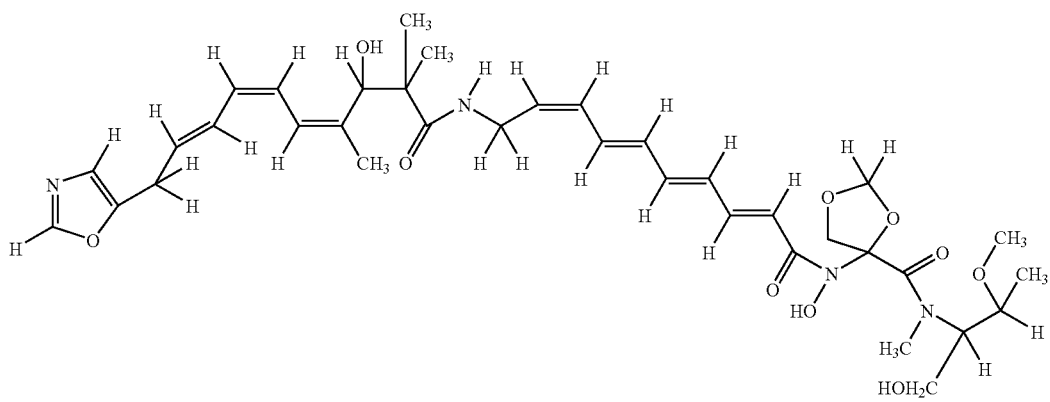

Compound 17

To a 0° C. solution of Compound 1 in dry tetrahydrofuran, is added slowly lithiumaluminum hydride and stirred overnight or until completion at room temperature. The reaction is quenched at 0° C. using saturated ammonium chloride and allowed to stir at room temperature for 1 hour. The reaction mixture is diluted with ethyl acetate and water and the layer separated. The organic layer is washed with brine, dried over magnesium sulfate, filtered and concentrated in vacuo. The residue is purified by silica gel column chromatography using a mixture of methanol and methylene chloride as eluent to give Compound 17.

EXAMPLE 11

Synthesis of Compound 23 from Oxidation of Compound 1

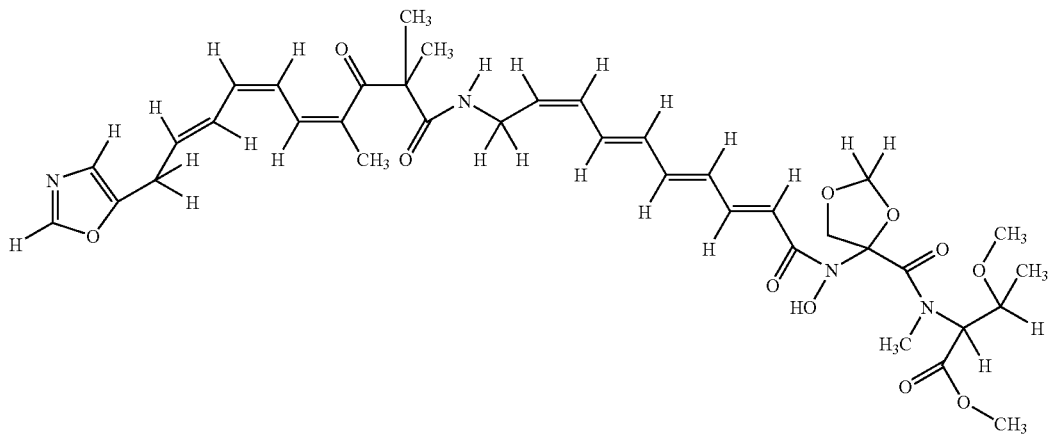

Compound 23

To a methylene choride solution of Dess-Martin periodinane is added a solution of Compound 1 in methylene chloride and the reaction stirred at room temperature for 1 hour. The mixture is diluted with diethyl ether and a saturated aqueous sodium bicarbonate solution containing sodium thiosulfate. Organic layer is separated and washed with saturated aqueous sodium bicarbonate, water and brine, dried over magnesium sulfate, filtered and concentrated in vacuo. The residue is purified by silica gel column chromatography using a mixture of methanol and methylene chloride as eluent to give Compound 23.

All patents, patent applications, and published references cited herein are hereby incorporated by reference in their entirety. While this invention has been particularly shown and described with reference to preferred embodiments thereof, it will be understood by those skilled in the art that various changes in form and details may be made therein without departing from the scope of the invention encompassed by the appended claims.

The invention claimed is:

1. A compound of the formula

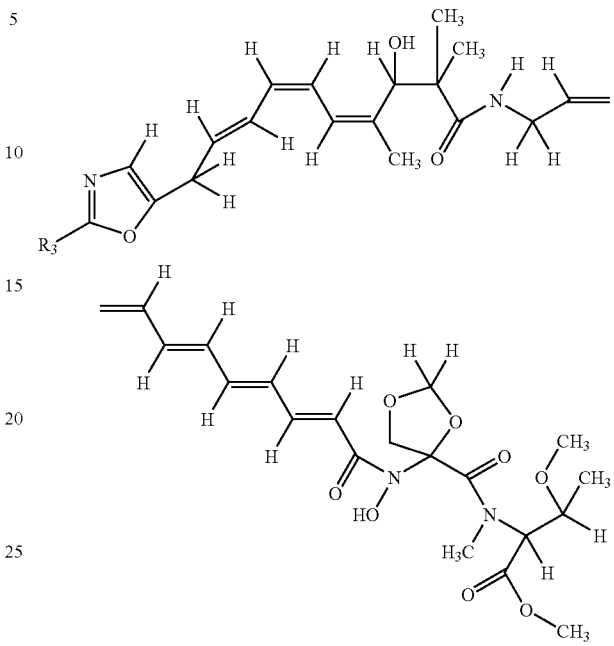

wherein $R_3$ is selected from H and methyl; or a pharmaceutically acceptable salt thereof.

2. A compound of the formula

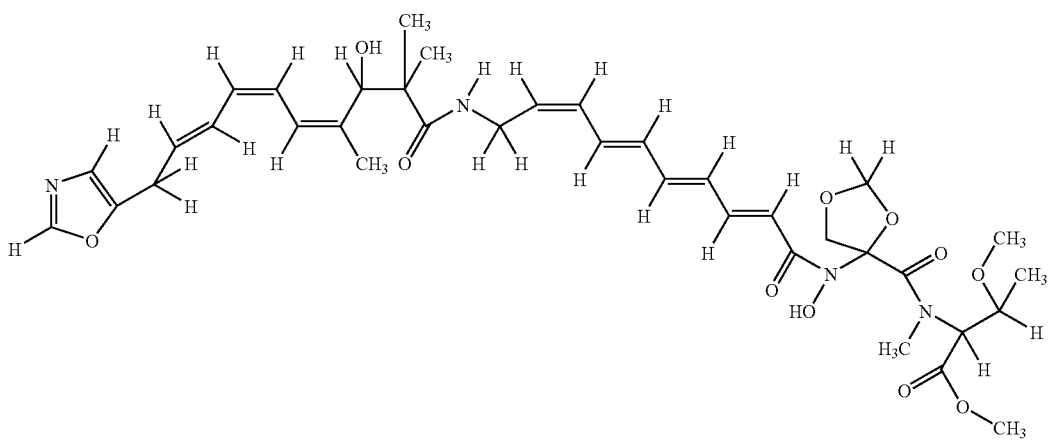

or a pharmaceutically acceptable salt thereof.

3. A compound of the formula

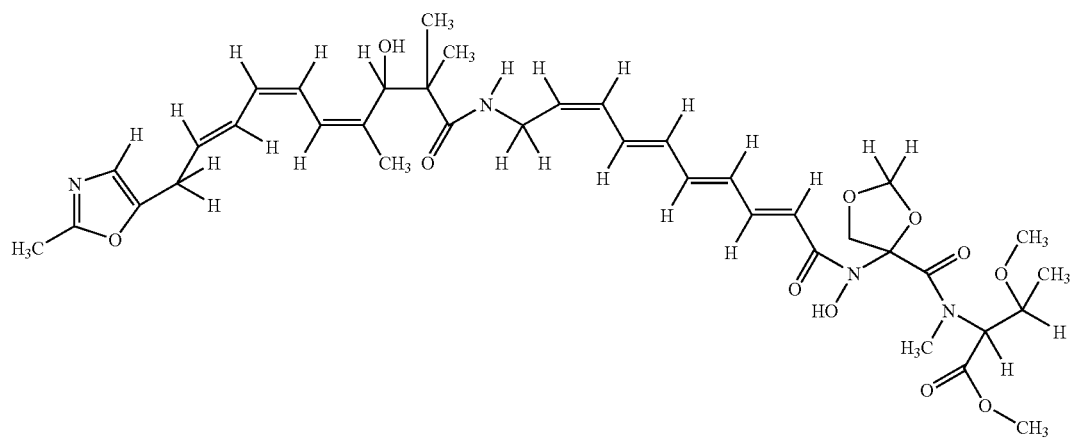

or a pharmaceutically acceptable salt thereof.

4. A pharmaceutical composition comprising compound of the formula

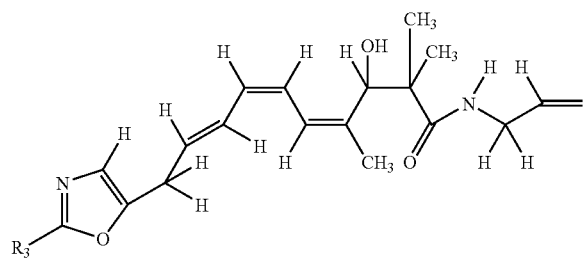

-continued

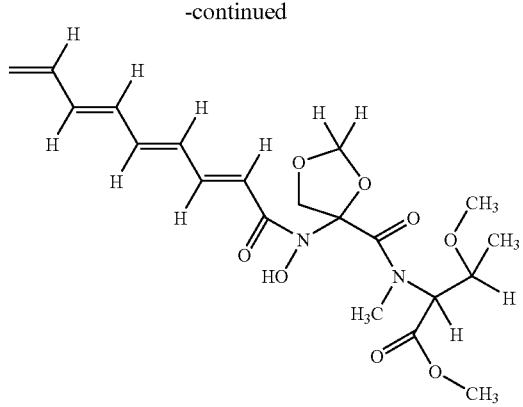

wherein $R_3$ is selected from H and methyl; or a pharmaceutically acceptable salt thereof, together with a pharmaceutically acceptable carrier.

5. A pharmaceutical composition comprising a compound of the formula

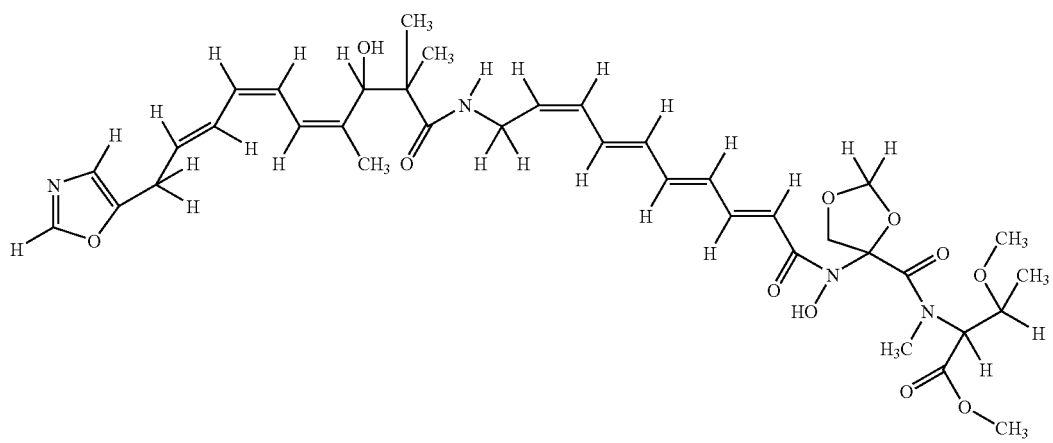

or a pharmaceutically acceptable salt thereof, together with a pharmaceutically acceptable carrier.

6. A pharmaceutical composition comprising a compound of the formula

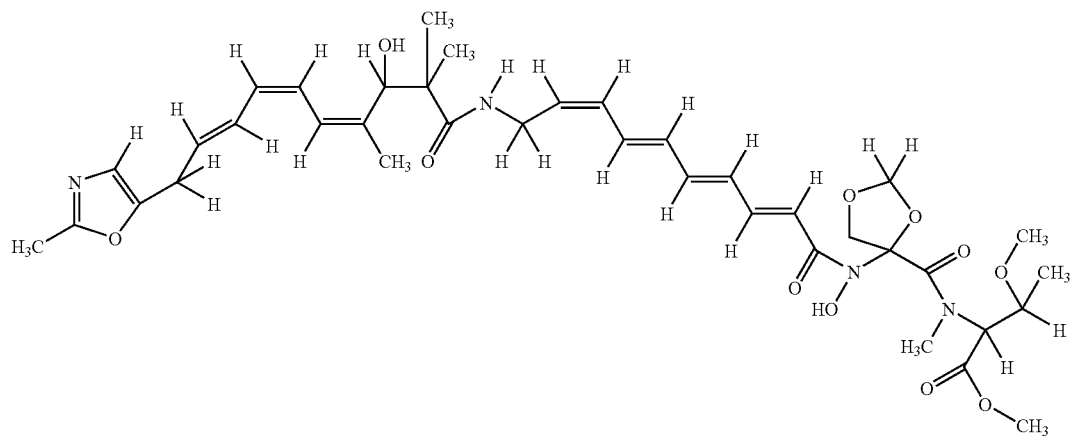

or a pharmaceutically acceptable salt thereof, together with a pharmaceutically acceptable carrier.

7. A polyene oxazole obtained by a method comprising
    (a) cultivating a *Streptomyces sparsogenes* strain, wherein said cultivation is performed under aerobic conditions in a nutrient medium comprising at least one source of carbon atoms and at least one source of nitrogen atoms; and
    (b) isolating a polyene oxazole from the strain cultivated in step (a), wherein said polyene oxazole is a compound of the formula

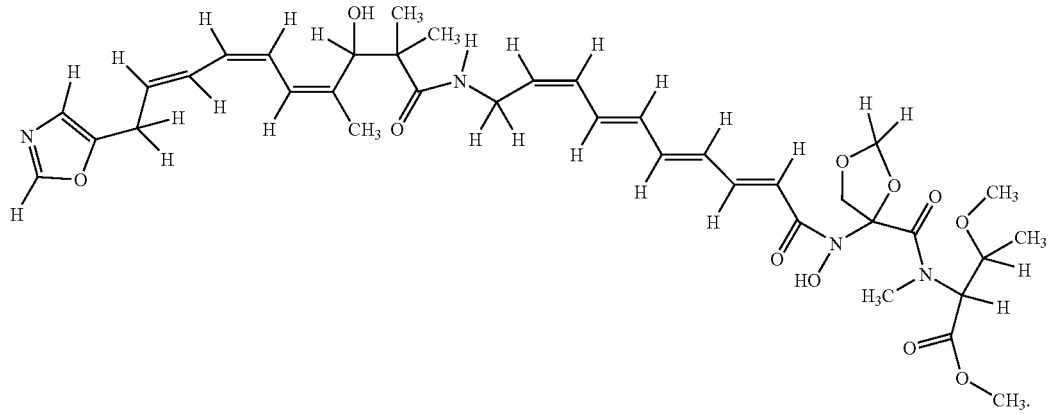

8. A polyene oxazole obtained by a method comprising
(a) cultivating a *Streptomyces sparsogenes* strain, wherein said cultivation is performed under aerobic conditions in a nutrient medium comprising at least one source of carbon atoms and at least one source of nitrogen atoms; and
(b) isolating a polyene oxazole from the strain cultivated in step (a), wherein said polyene oxazole is a compound of the formula

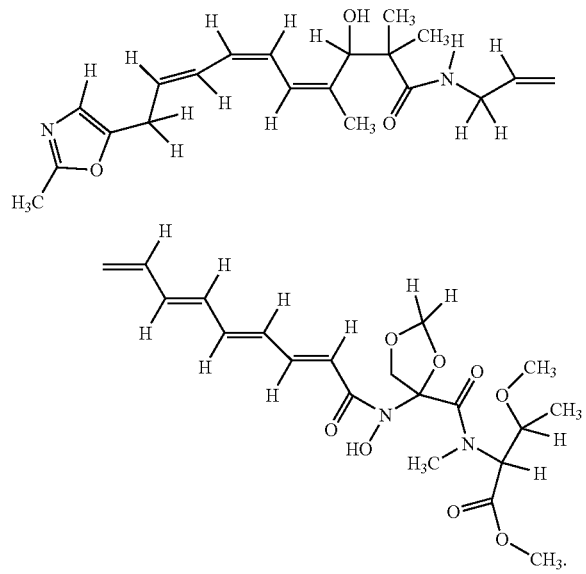

9. A process for making the compound of claim 1, comprising the steps of cultivation of a *Streptomyces sparsogenes* strain, in a nutrient medium comprising at least one source of carbon atoms and at least one source of nitrogen atoms, and isolation and purification said compound.

10. The process of claim 9, wherein said *Streptomyces sparsogenes* strain is NRRL 2940 or a mutant thereof.

11. The process of claim 10, wherein said mutant is strain [S03]022 (deposit accession number IDAC 270504-04).

12. The process of claim 9 wherein cultivation occurs under aerobic conditions.

13. The process of claim 9 wherein said nutrient medium is a media selected from the group consisting of media DA, DZ, ET, JA, MY, NA, QB and VB as set forth in the table below:

| Component | DA | DZ | ET | JA | MY | NA | QB | VB |
|---|---|---|---|---|---|---|---|---|
| Glucose | 10 | 5 | | | | | 6 | 10 |
| Sucrose | | | | | | | | 20 |
| Maltose | | | | 4 | | | | |
| Cane molasses | 10 | 10 | 60 | | | 10 | | 20 |
| Soluble starch | 5 | 15 | 20 | | | | 5 | |
| Corn starch | | | | 30 | | | | |
| Potatoe dextrin | 20 | | | | | | | |
| Corn steep solids | 5 | | | | | | 2.5 | |
| Corn steep liquid | | | | 15 | | | | |
| Malt extract | | | | | 35 | 10 | | |
| Yeast extract | | | | | | 4 | | |
| Pharmamedia | | | | | 15 | | 5 | |
| Glycerol | 10 | | | | | 20 | | |
| Soybean flour | 5 | | | | | | | |
| Soytonpeptone | | | | | | | | 5 |
| Fish meal | | | 10 | 20 | | | | |
| Bacto-peptone | | | | | | 1 | | |
| MgSO$_4$•7H$_2$O | 0.5 | | | | | | | |
| CaCO$_3$*[1] | 3 | 5 | 2 | 2 | | 4 | | 2.5 |
| FeCl$_2$•4H$_2$O | 0.1 | | | | | | | |
| NaI | | | | 0.5 | | | | |
| ZnCl$_2$ | 0.1 | | | | | | | |
| MnCl$_2$•4H$_2$O | 0.1 | | | | | | | |
| CuSO$_4$•5H$_2$O | | | | 0.1 | | | | |
| Phytic acid | 1 | | | | | | | |
| Casamino acid | | | | | | 5 | | |
| Porflo oil | | | | | | | 2 | |

Ingredients are in gm/L The pH is adjusted to 7 except where indicated
*[1] pH adjusted to 7.3 prior to the addition of CaCO$_3$.

14. The process of claim 9 wherein said cultivation is carried out at a temperature ranging from 18° C. to 40° C.

15. The process of claim 9 wherein said cultivation is carried out at a pH ranging from 6 to 9.

16. *Streptomyces sparsogenes* having IDAC accession number 270504-04.

* * * * *